United States Patent
Iino et al.

(10) Patent No.: US 6,952,072 B2
(45) Date of Patent: Oct. 4, 2005

(54) ULTRASONIC MOTOR AND ELECTRONIC APPARATUS UTILIZING ULTRASONIC MOTOR

(75) Inventors: Akihiro Iino, Chiba (JP); Satoshi Watanabe, Chiba (JP); Masao Kasuga, Chiba (JP); Makoto Suzuki, Chiba (JP)

(73) Assignee: Seiko Instruments Inc., Chiba (JP)

( * ) Notice: Subject to any disclaimer, the term of this patent is extended or adjusted under 35 U.S.C. 154(b) by 0 days.

(21) Appl. No.: 10/281,021

(22) Filed: Oct. 25, 2002

(65) Prior Publication Data

US 2003/0164659 A1 Sep. 4, 2003

(30) Foreign Application Priority Data

Nov. 9, 2001 (JP) ........................................ 2001-345243
Nov. 14, 2001 (JP) ........................................ 2001-348864

(51) Int. Cl.[7] .............................................. H02N 2/12
(52) U.S. Cl. ................................................. 310/323.04
(58) Field of Search ........................ 310/323.04, 323.12, 310/323.13, 325, 366

(56) References Cited

U.S. PATENT DOCUMENTS

| | | | | |
|---|---|---|---|---|
| 5,410,204 A | * | 4/1995 | Imabayashi et al. | ... 310/323.13 |
| 6,018,213 A | * | 1/2000 | Yano | ...................... 310/323.12 |
| 6,037,702 A | * | 3/2000 | Tamai | .................... 310/323.06 |
| 6,166,477 A | * | 12/2000 | Komoda et al. | ....... 310/323.13 |
| 6,300,705 B1 | * | 10/2001 | Komoda et al. | ....... 310/323.12 |
| 6,366,004 B1 | * | 4/2002 | Yano et al. | ............. 310/323.12 |
| 6,469,419 B2 | * | 10/2002 | Kato et al. | ............. 310/323.02 |
| 6,509,673 B2 | * | 1/2003 | Komoda | ................. 310/323.12 |

* cited by examiner

Primary Examiner—Thomas M. Dougherty
(74) Attorney, Agent, or Firm—Adams & Wilks

(57) ABSTRACT

An ultrasonic motor has a piezoelectric vibrator driven by a voltage signal to undergo expansion and compression movement. At least two elastic bodies are connected to opposite ends of the piezoelectric vibrator and are vibrationally driven by the expansion and compression movement of the piezoelectric vibrator. Each of the elastic bodies has at least one groove formed in a surface thereof for converting the expansion and compression movement of the piezoelectric vibrator into torsional vibration so that the elastic bodies generate a combination of longitudinal vibration and torsional vibration. A movable member is connected to the elastic bodies to be frictionally driven by the combination of longitudinal and torsional vibrations generated by the elastic bodies.

30 Claims, 25 Drawing Sheets

Vibration Modes

Colpitts Oscillation Circuit

Frequency/Admittance Characteristics of the Stator

ULTRASONIC MOTOR AND ELECTRONIC APPARATUS UTILIZING ULTRASONIC MOTOR

BACKGROUND OF THE INVENTION

1. Field of the Invention

The present invention relates generally to a configuration of a Langevin-type ultrasonic motor, particularly a rod-type ultrasonic motor in which a longitudinal vibration is combined with a torsional vibration, to a system for driving the ultrasonic motor, and to an electronic apparatus utilizing the ultrasonic motor.

2. Description of the Related Art

A conventional rod-type ultrasonic motor has a vibrating body provided with an elastic body for generating a longitudinal vibration and an elastic body for generating a torsional vibration. Drive voltages whose phases are different from each other are applied to the respective elastic bodies to excite the vibrating body, and the force in a torsional direction produced when the vibrating body undergoes an expanding motion caused by combined longitudinal-torsional vibrations is transmitted to a rotor.

In addition to foregoing conventional ultrasonic motor, a standing-wave ultrasonic motor has been proposed in which inclined slit grooves are formed on a vibrating body, torsional vibrations are generated from longitudinal vibrations of a piezoelectric vibrator, and a rotor is rotated by elliptic vibrations that are generated through combination of the longitudinal vibrations and the torsional vibrations.

In other words, when the vibrating body whose surface is in contact with the rotor generates combined longitudinal-torsional vibrations, the force in a torsional direction produced when the vibrating body undergoes an expanding motion is transmitted to the rotor. However, the force in the torsional direction produced when the vibrating body undergoes a contracting motion is not transmitted to the rotor due to reduced frictional force. Hence, the rotor is driven unidirectionally.

Such a conventional ultrasonic motor provided with an elastic body for generating longitudinal vibrations and an elastic body for generating torsional vibrations has a problem in that its configuration and a circuit for supplying electricity are complicated, which results in high cost or a large outer dimension. However, such a conventional ultrasonic motor has a function of controlling the number of revolutions and torque without restraint and thus has an advantage of being adaptable to a wide range of uses.

For instance, a conventional ultrasonic motor shown in FIG. 5 has a standing-wave system. According to this conventional example, there are provided an ultrasonic motor that can rotate bidirectionally with a single phase and a method of driving the ultrasonic motor.

In this ultrasonic motor, elliptic vibrations that are generated through combination of longitudinal vibrations and torsional vibrations are caused at the end face of a vibrating body 120 and thereby a rotor 110 is driven to rotate. The ultrasonic motor includes vibration generation means 122, 124, inclined slit grooves 138, and a voltage application means 150. The vibration generation means 122, 124 generate longitudinal vibrations with a longitudinal resonance frequency or torsional vibrations with a torsional resonance frequency of the vibrating body 120 according to the AC voltage with a frequency to be applied thereto. The inclined slit grooves 138 allow one of a longitudinal vibration and a torsional vibration to be generated from the other and allow them to be combined to generate an elliptic vibration. The voltage application means 150 is different from the two vibration generation means 122, 124 in polarizing direction and selectively switches AC voltages with frequencies corresponding to a longitudinal vibration and a torsional vibration to apply one thus selected.

The vibration generation means 122, 124 generate longitudinal vibrations with a longitudinal resonance frequency or torsional vibrations with a torsional resonance frequency of the vibrating body 120 so that the vibrating body 120 vibrates considerably. In order to generate longitudinal vibrations in the vibrating body 120, a frequency corresponding thereto is selected and an AC voltage with the selected frequency is applied to the vibration generation means 122, 124 by the voltage application means 150. Then torsional vibrations are generated from the longitudinal vibrations generated in the vibrating body 120 through the grooves 138 that are vibration conversion means. Subsequently, the two vibrations are combined to cause elliptic vibrations at the end face of the vibrating body and thereby the rotor rotates. In order to generate torsional vibrations in the vibrating body 120, a frequency corresponding thereto is selected and an AC voltage with the selected frequency is applied to the vibration generation means 122, 124 by the voltage application means. Then longitudinal vibrations are generated from the torsional vibrations generated in the vibrating body 120 through the grooves 138 that are vibration conversion means. Subsequently, the two vibrations are combined to cause elliptic vibrations at the end face of the vibrating body and thereby the rotor rotates. That is, the rotational directions are switched through the use of the fact that the direction of rotation caused when longitudinal vibrations are converted to torsional vibrations is reversed when torsional vibrations are converted to longitudinal vibrations and vice versa.

This switching of rotational directions is operated through switching of frequencies of voltages to be applied to the vibration generation means 122, 124. With respect to these frequencies, a primary resonance frequency of longitudinal vibrations is 55 kHz and a secondary resonance frequency of torsional vibrations is 63 kHz. In other words, this ultrasonic motor has resonance points in modes whose frequencies are different from each other by 8 kHz. Hence, the ultrasonic motor has problems in that due to variations in the two resonance frequencies caused in the production process, variations in characteristics of the ultrasonic motor are caused or two vibration modes influence each other and thereby output power is compelled to be reduced.

Furthermore, there is a problem in that vibrations are unstable, and an ultrasonic motor of a self-oscillation type has difficulty in operational stability. In order to drive this ultrasonic motor, a voltage application unit having a frequency tracking function is required separately. Furthermore, two piezoelectric vibrators are required that are different from each other in polarizing direction. Consequently, there has been a problem in that a size reduction is difficult due to its configuration. If the size reduction is forcibly achieved, power is reduced to an extreme degree.

A Langevin-type ultrasonic motor has a configuration in which a piezoelectric vibrator is sandwiched between rod-like elastic bodies from its both sides. In this Langevin-type ultrasonic motor, while the piezoelectric vibrator is sandwiched between the rod-like elastic bodies from both sides, electrode plates for supplying electricity to the piezoelectric vibrator are required. In addition, it is necessary to convey the torque of the rotor to the outside while maintaining the state where the rotor is in press contact with the elastic body in the end portion of the piezoelectric vibrator. Hence, this kind of ultrasonic motor has to have a complicated support structure and conduction structure and thus it has been difficult to achieve a further size reduction.

This type of Langevin-type ultrasonic motor is shown in FIG. 9 and which includes an ultrasonic motor 16 having a columnar rotor 28 attached with a center shaft 30, a pipe 12, and a holder 14.

The support structure of the conventional ultrasonic motor shown in FIG. 9 is formed with the ultrasonic motor 16 contained inside the pipe 12 and with an end portion of the pipe 12 attached to the holder 14 rotatably. A support member 36 is inserted loosely into a hollow portion formed of a hole made from one end of the center shaft 30 to a portion corresponding to nodes in a torsional vibration mode, and the tip of the support member 36 is fixed to the bottom part of the hollow portion. The other end face of the support member 36 is attached to the inner surface of the holder 14 and the rotor is fixed to the inner surface of the pipe.

In the ultrasonic motor having such a configuration, it is necessary to create the hollow portion formed of a hole made to reach the portion corresponding to nodes and to fix the tip of the support member and the bottom part of the hollow portion to each other. Due to its configuration that requires joining of the rotor and the pipe, the supply of electricity to a piezoelectric vibrator, which is not shown in the drawing, and the like, the manufacturing process is complicated. Hence, it is difficult to achieve a further size reduction. If a size reduction is forcibly achieved, there is a possibility that the structures of portions providing support, pressing forces, and conduction may be stressed, and thereby energy loss may result.

SUMMARY OF THE INVENTION

In order to solve the above-mentioned problems in the conventional art, it is an object of the present invention to provide an ultrasonic motor having less variations and high output power by allowing the frequency with a resonance point at which the admittance value is minimum and that with a resonance point adjacent thereto to be apart from each other in the frequency-impedance characteristics of a vibrating body.

In addition, it is also an object of the present invention to provide an ultrasonic motor that employs only a piezoelectric vibrator having a unidirectional polarization structure, which can be driven by a self-oscillation mode that requires no voltage application unit for driving the vibrating body, and thereby allows a reduction in its size to be achieved.

Furthermore, the present invention is also intended to provide an ultrasonic motor that is allowed to have a further reduced size by providing structures giving support, pressing forces, and conduction that are not subjected to any stress, for a Langevin-type ultrasonic motor having a vibrating body including a piezoelectric vibrator and elastic bodies.

The present invention is characterized by including grooves in an ultrasonic motor in which a movable body is driven by vibrations of a vibrating body including a piezoelectric vibrator and elastic bodies provided on and under the piezoelectric vibrator. These grooves are provided in regions corresponding to nodes of standing waves that are stress concentration zones so as to cause large torsional displacement.

In the present invention, the grooves are provided in places other than upper and lower faces of the elastic bodies, and the elastic bodies have grooves provided at a smaller angle than 90 degrees at least in a part, respectively. In addition, the grooves are provided as a plurality of grooves formed at a fixed angle, the grooves are provided spirally around the elastic bodies at least once, and the grooves are provided at the same angle to be located symmetrically in the longitudinal direction with respect to the center of a stator.

An ultrasonic motor according to the present invention is a Langevin-type ultrasonic motor that drives a rotor by vibrations of a vibrating body having elastic bodies on both sides of a piezoelectric vibrator sandwiched therebetween. The ultrasonic motor is characterized in that the piezoelectric vibrator has a projecting part that projects in the radial direction of the vibrating body and the projecting part is used as means for preventing rotation of the vibrating body in combination with the shape of the cross section in the axis direction of a casing.

The projecting part functions as a member for restricting the radial displacement of the vibrating body in combination with the inner wall surface of the casing. Furthermore, the projecting part functions as a member that carries pressing forces exerted by the elastic body disposed in the end portion of the casing in combination with a stepped portion formed on the inner wall of the casing.

In the present invention, a piezoelectric vibrator is used that is one obtained through cutting a plate-like piezoelectric element into a rectangular shape.

The piezoelectric vibrator has electrodes made of deposition films formed on both surfaces of the piezoelectric element and a projecting part that projects in the radial direction of the vibrating body. In the piezoelectric vibrator, a lead wire used for applying a drive voltage is connected directly to the projecting part. Furthermore, the present invention employs a configuration that ensures a contact between the end face of the vibrating body and the surface of the rotor under pressing forces by means of the elastic member disposed in the end portion of the casing.

BRIEF DESCRIPTION OF THE DRAWINGS

In the accompanying drawings:

FIG. 8A is a perspective view showing a basic configuration of its stator, FIG. 8B is a sectional view of the whole structure, and FIG. 8C is a sectional view taken along line c–c shown in FIG. 8B.

DETAILED DESCRIPTION OF THE PREFERRED EMBODIMENTS

Figure 1A:
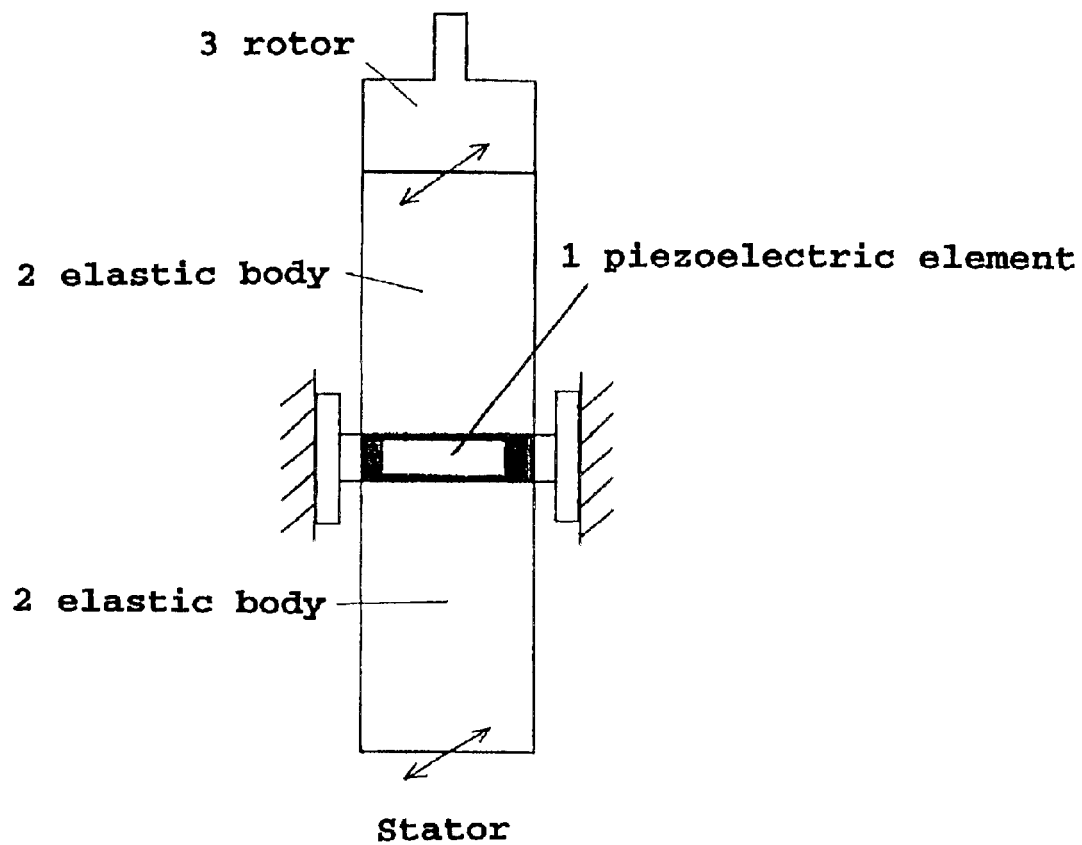
FIG. 1A is a drawing showing a basic structure of a stator in an ultrasonic motor according to the present invention.
Figure 1B:
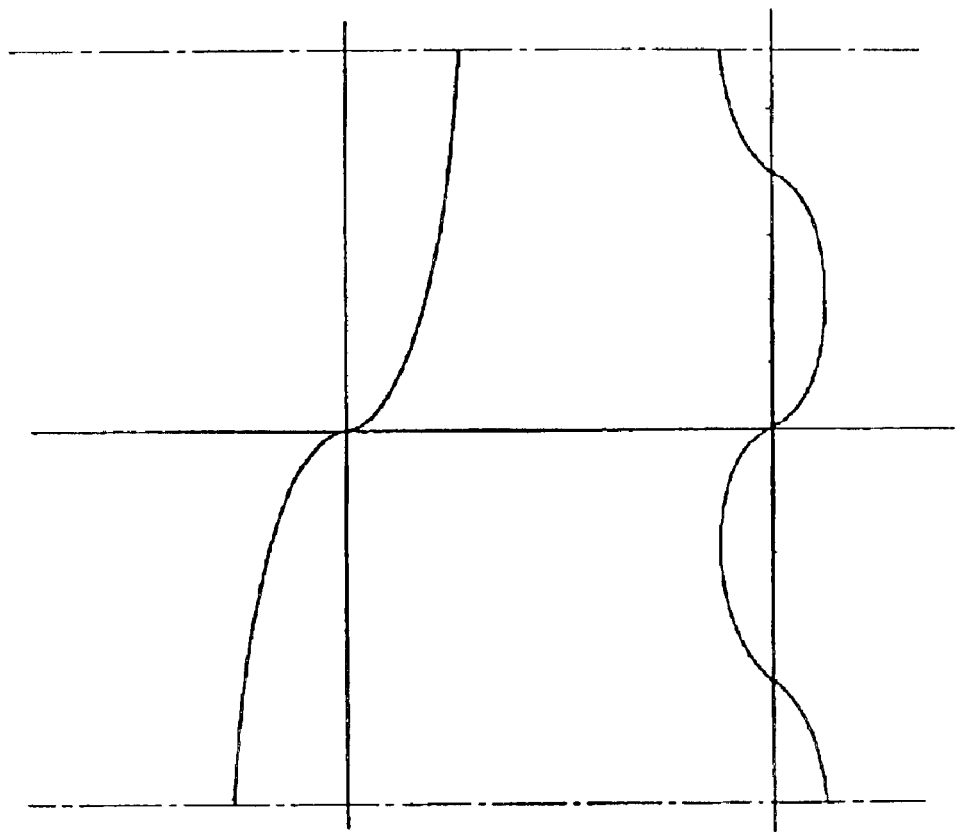
FIG. 1B is a graph used for explaining a standing-wave vibration mode of the ultrasonic motor.

FIGS. 1A and 1B show a drawing and a graph used for explaining a basic structure and a standing-wave vibration mode of a vibrating body in an ultrasonic motor according to the present invention.

The ultrasonic motor of the present invention drives a rotor 3 by vibrations of a vibrating body composed of a piezoelectric vibrator 1 formed of a piezoelectric element and two elastic bodies 2 provided on and under the piezoelectric vibrator 1 as shown in FIG. 1A. This drive principle is as follows: groove portions are formed in the elastic bodies 2 to convert longitudinal vibrations (i.e., expansion and compression) of the piezoelectric vibrator 1 into torsional vibrations and to allow the vibrating body to generate combined longitudinal-torsional vibrations indicated with arrows in FIG. 1A, and thereby rotational force is applied to the rotor by the motion (such as an elliptical motion or the like) of the end face of the vibrating body.

Depending on the vibration mode to be used, the direction of the arrows is changed oppositely and thereby the rotor rotates in reverse. In order to cause large and stable torsional component displacement in the vibrating body, the present invention employs a configuration in which each of the two elastic bodies disposed on both sides of the piezoelectric vibrator are provided with grooves at a smaller angle than 90 degrees.

The grooves provided for the elastic bodies disposed on both sides are formed to be located symmetrically with respect to the center in the longitudinal direction of the vibrating body with considerations given to motion balance. In addition, they are formed in the same direction at the same tilt angle to allow the phases of the torsional components generated in the respective elastic bodies to coincide with each other.

This permits the elastic bodies disposed on both sides of the piezoelectric vibrator 1 located in the middle to vibrate in the same mode. Hence, the vibrating body as a whole produces one combined longitudinal-torsional vibration and thus a large torsional vibration component can be obtained.

The vibrations become simple and thereby spurious vibrations are not generated easily. Hence, no resonance point of frequencies that are close to each other exists, and different vibrations do not influence each other in the case of excitation at a predetermined frequency. This is a big advantage and a characteristic of the present invention.

FIG. 1B is a graph showing examples of vibration modes (a primary mode and a secondary mode) in the case where standing-waves are generated in the vibrating body in resonance with the excitation at a predetermined frequency. Of course, vibration modes with higher orders may be used. It was found that in such vibrations, large torsional displacement was caused when grooves were provided for regions corresponding to nodes of the standing waves that were stress concentration zones. Based on this knowledge, in the present invention, the groove portions are provided so as to be located in regions corresponding to nodes of the standing waves according to the vibration mode thereof.

It also was found that with respect to the position of the piezoelectric vibrator, it was not limited to the central part, and a high torque was obtained when the piezoelectric vibrator was disposed in regions corresponding to nodes in the vibrating body undergoing combined longitudinal-torsional vibrations. When the piezoelectric vibrator is disposed in a location other than the central part, two piezoelectric vibrators are provided to be located symmetrically with respect to the center of the vibrating body.

The employment of the configurations described above allows high torque outputs to be obtained. Hence, it is not necessary to use the complicated configuration shown in the conventional example in which piezoelectric vibrators whose polarizing directions are different from each other are stacked to provide large longitudinal vibrations and voltages with different phases are applied to drive piezoelectric vibrators. Thus, the configuration is simplified and thereby a further size reduction can be achieved.

With respect to the frequency characteristics of the vibrating body, values of resonance frequencies adjacent to each other are considerably apart from each other. Hence, stable standing waves can be generated in the vibrating body. This enables the piezoelectric vibrator to be driven by self-oscillation. As a result, it is not necessary to prepare means for applying voltages with frequencies for excitation separately, which is effective in achieving a reduction in size of the system.

The same circuit as one for quartz vibrators commonly used in, for example, watches can be used as the driving circuit for this self-oscillation without being modified.

Figure 2A:
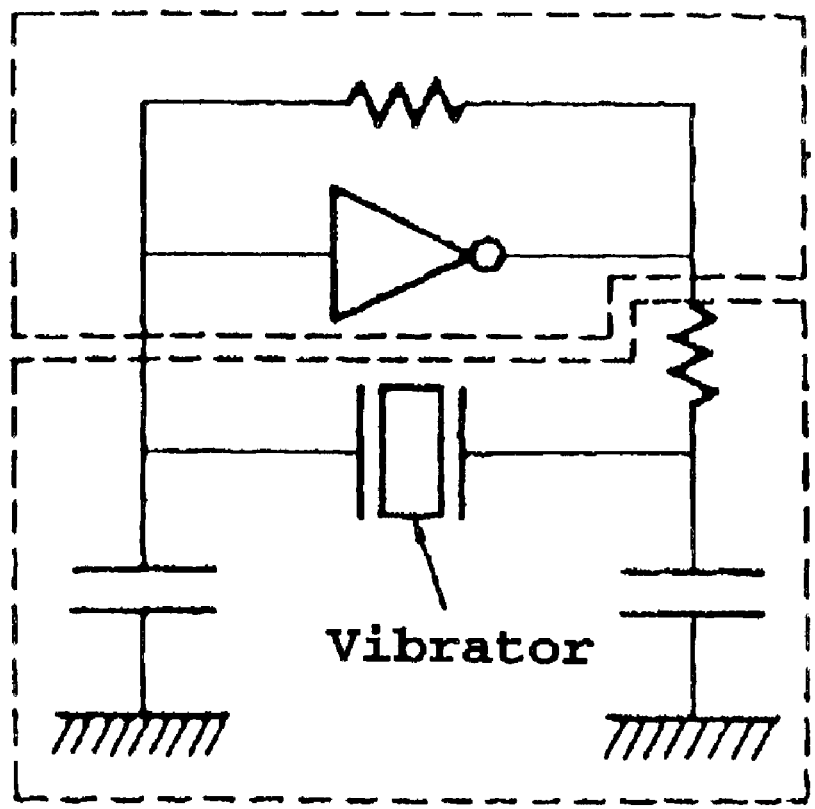
FIG. 2A is a drawing showing a Colpitts oscillation circuit used for allowing a piezoelectric element according to the present invention to undergo self-excited vibrations as a vibrator of the oscillation circuit.
Figure 2B:
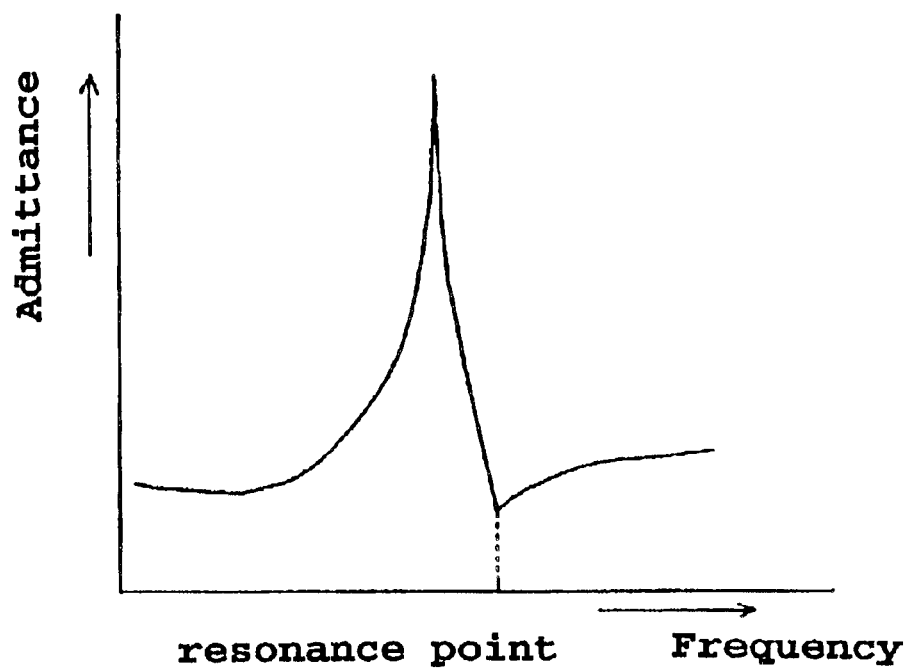
FIG. 2B is a graph showing frequency/admittance characteristics of the stator according to the present invention.

FIG. 2A shows a Colpitts oscillation circuit. The vibrator used in the circuit is not quartz but a piezoelectric vibrator for driving. The graph shown in FIG. 2B illustrates the frequency/admittance characteristics of the vibrating body according to the present invention. Since the resonance points adjacent to each other have considerably different frequencies, stable standing waves can be produced in the vibrating body, variations in characteristics are small, and high torque is obtained, which are advantages.

Embodiment 1

FIG. 3 shows a plurality of embodiments of vibrating bodies used in the present invention.

Figure 3A:
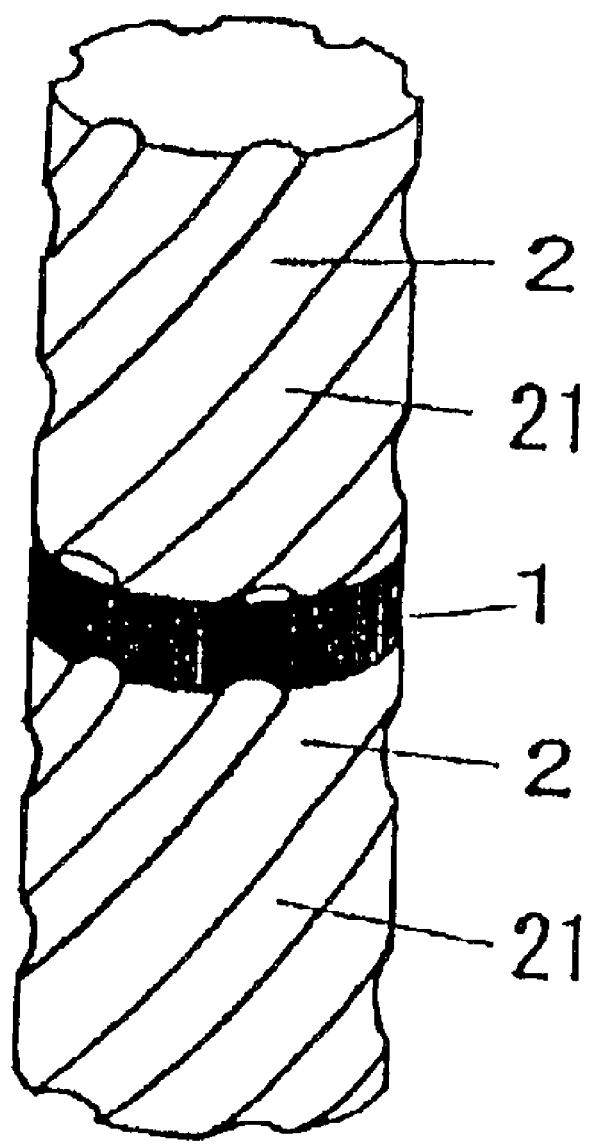
FIGS. 3A to 3J are drawings showing examples of vibrating body models employed in the present invention.

In the embodiment shown in FIG. 3A, a plurality of spiral grooves 21 are formed on surfaces of columnar elastic bodies 2 that are disposed on and under a piezoelectric vibrator 1 formed of a piezoelectric element located at the center so as to sandwich the piezoelectric vibrator 1.

The grooves 21 provided for the upper elastic body and the grooves 21 provided for the lower elastic body are formed to be identical in the number, direction, and angle. That is, identical members can be used for the upper and lower elastic bodies 2. Since this embodiment has high structural uniformity, the elastic bodies 2 have no stress concentration zone and thus this embodiment has excellent characteristics in terms of fatigue resistance and crashworthiness. Furthermore, the rate of conversion into torsional displacement is high and thereby a motor to be driven at high speed can be obtained. In addition, since the grooves are provided overall, this embodiment is also excellent in exciting the secondary mode.

Figure 3B:
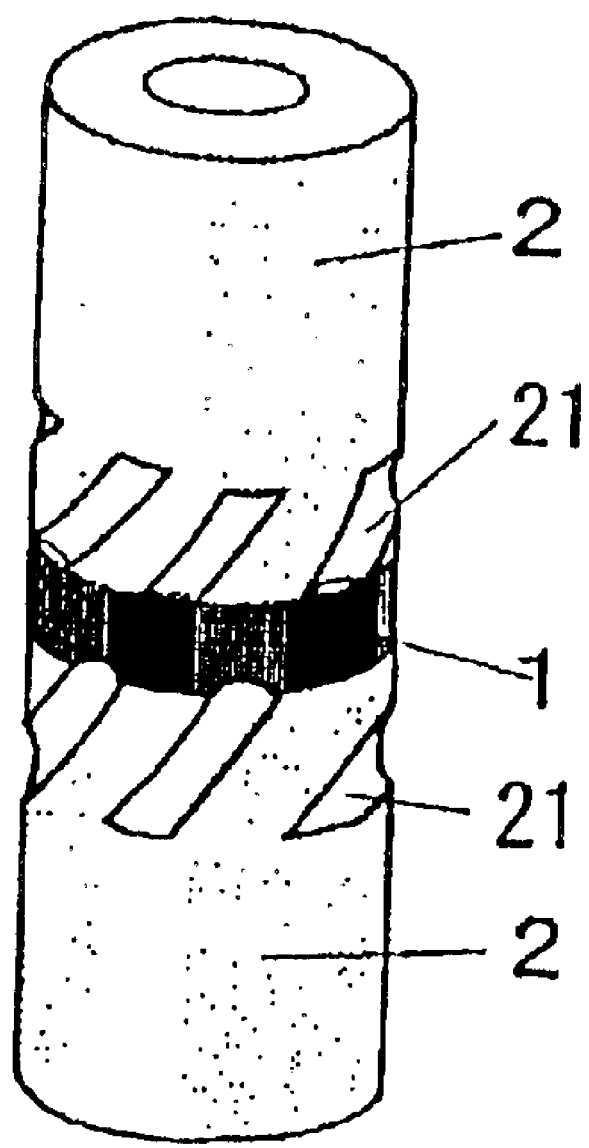

In the embodiment shown in FIG. 3B, cylindrical elastic bodies are used that are provided with a space at their center portion and a plurality of spiral grooves 21 are provided at the surfaces of these upper and lower elastic bodies 2 but only in the vicinities of the end portions that are in contact with a piezoelectric vibrator 1.

In this embodiment, the grooves are provided in regions corresponding to nodes of vibrations. Hence, this embodiment is excellent in terms of high torsion conversion rate and thus is suitable for the use in a high-speed drive motor. In addition, since no groove is provided in the portion that comes into contact with a rotor, this embodiment is also excellent in resistance to the wear caused between the rotor as a movable body and the elastic body 2 functioning as a member for transmitting torque.

Figure 3C:
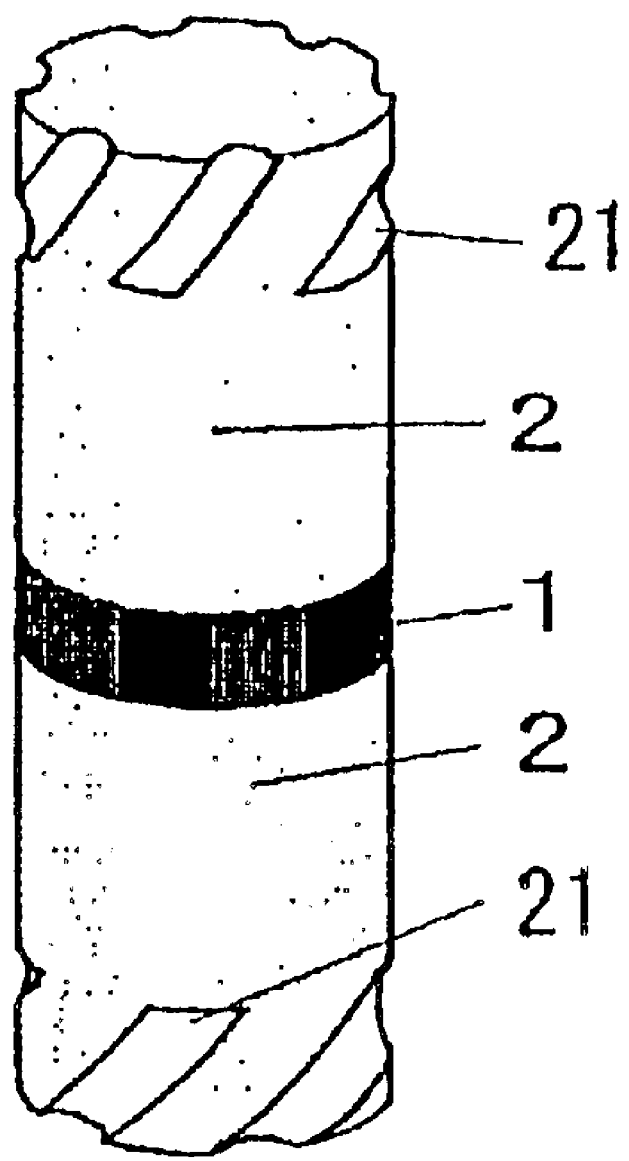

In the embodiment shown in FIG. 3C, columnar elastic bodies are used and a plurality of spiral grooves 21 are provided for the surfaces of these upper and lower elastic bodies 2 but only in the vicinities of the respective outer end portions.

This embodiment is characterized in that the piezoelectric element used as the piezoelectric vibrator 1 has very high output transmission efficiency and output with high torque can be obtained. This is because since the whole surfaces of the elastic bodies and the piezoelectric vibrator are in contact with each other, a vibrating body is obtained that can transmit the displacement in the longitudinal direction of the piezoelectric element that produces torque efficiently and has a high electromechanical coupling coefficient.

Figure 3D:
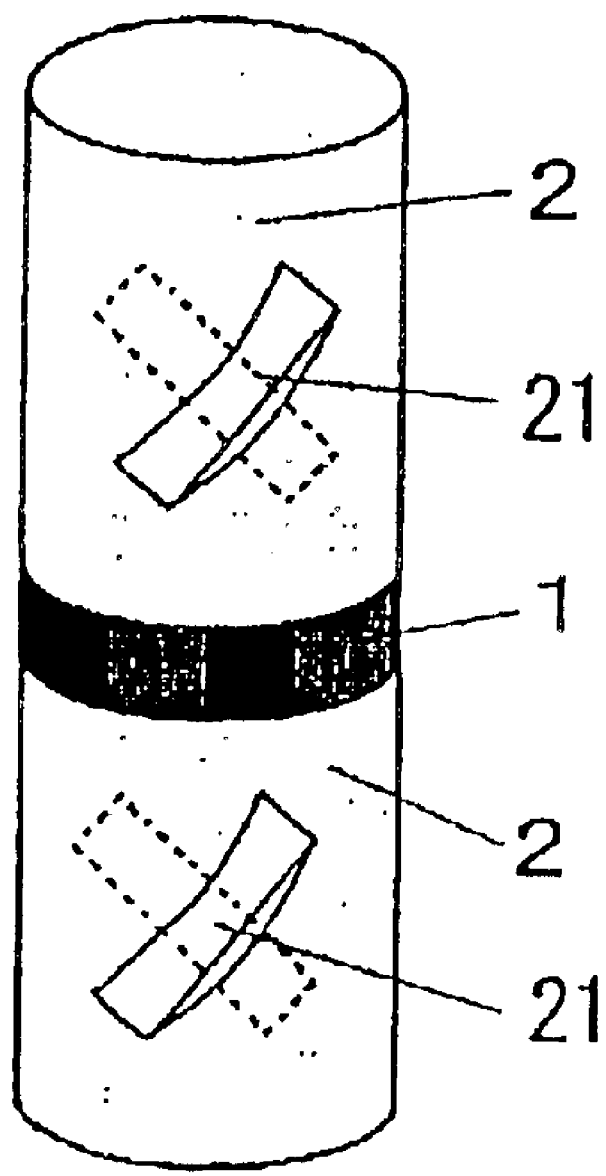

In the embodiment shown in FIG. 3D, columnar elastic bodies are used, and a plurality of grooves 21 are provided for the surfaces of the middle portions of the upper and lower elastic bodies 2 at the same angle in the same direction at intervals of 180 degrees or 90 degrees in the circumferential direction. The grooves 21 are provided at a smaller angle than 90 degrees with respect to a reference plane that is orthogonal to the direction of the axis of the elastic bodies.

These grooves are formed by a slitting process in which the side faces of the elastic bodies 2 are processed to be provided with planar slits. Hence, the middle portion in the longitudinal direction of each groove is the deepest portion when measured from the surface. This embodiment is excellent in terms of fatigue resistance, crashworthiness, working easiness, efficiency of transmitting output from the vibrator, high torque, and resistance to the wear caused between the rotor and vibrating body.

Figure 3E:
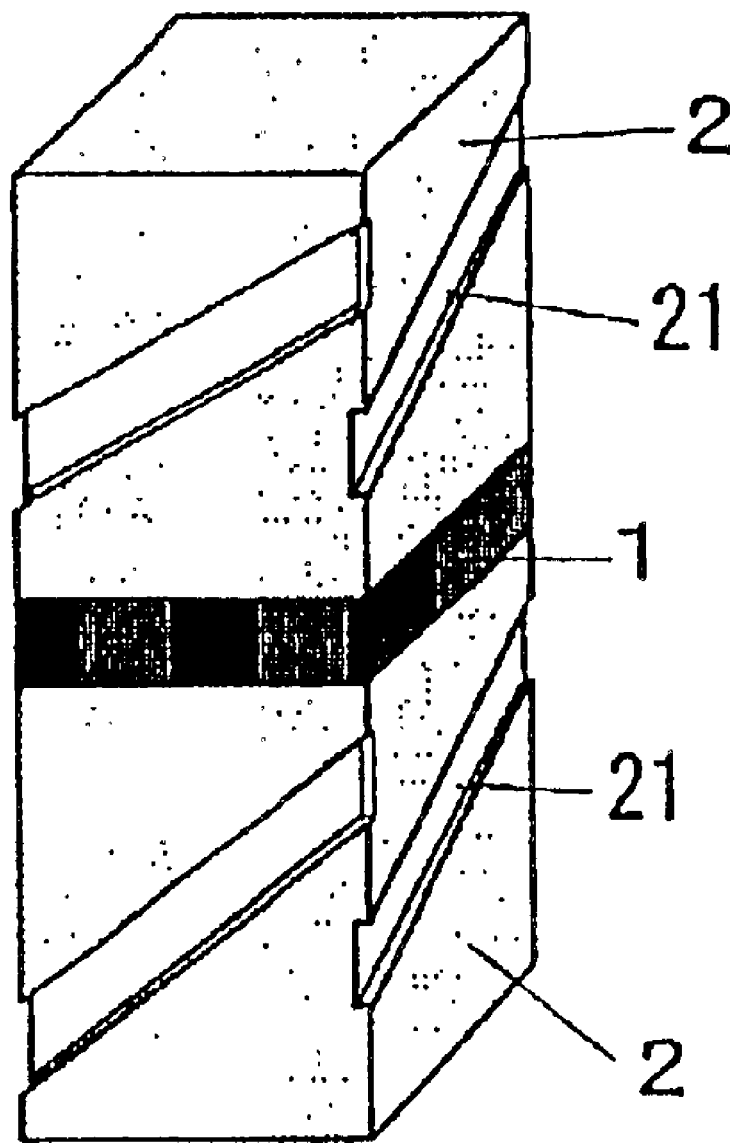

In the embodiment shown in FIG. 3E, square-pole-like elastic bodies are used, and grooves 21 are provided for the surfaces of the elastic bodies 2 at a smaller angle than 90 degrees and are provided for the center portions of the respective surfaces of the square pole at the same angle in the same direction.

These grooves are formed by a slitting process in which the side faces of the square pole members are processed to be provided with planar slits. Since the surfaces of the elastic bodies 2 are planar surfaces, the grooves have a uniform depth. Identical members can be used for the upper and lower elastic bodies 2. As in the case of the embodiment shown in FIG. 3D, this embodiment is also excellent in terms of fatigue resistance, crashworthiness, working easiness, efficiency of transmitting output from the vibrator, high torque, and resistance to the wear caused between the rotor and vibrating body.

Figure 3F:
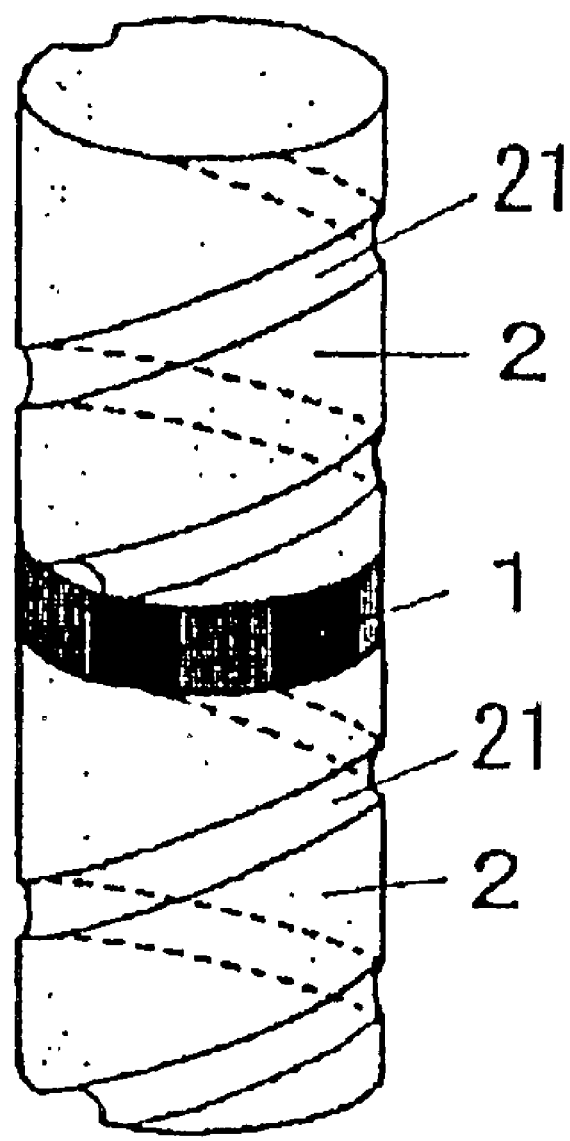

In the embodiment shown in FIG. 3F, columnar elastic bodies are used, and spiral grooves 21 provided for the surfaces of the upper and lower elastic bodies 2, respectively, at a smaller angle than 90 degrees are formed around their circumferential surfaces at least once.

In the case of using this embodiment, when compared to the case of using vibrating bodies provided with a plurality of grooves, individual products have less variations in performance and the spurious vibration is not generated easily. The spiral groove 21 in the upper elastic body and the spiral groove 21 in the lower elastic body are formed so as to be identical to each other in terms of the number, direction, and angle. Hence, identical members can be used for the upper and lower elastic bodies 2. Since this embodiment has high structural uniformity, the elastic bodies 2 have no stress concentration zone. This embodiment therefore is characterized in having excellent fatigue resistance and crashworthiness.

In addition, this embodiment is effective for secondary mode excitation and is also excellent in terms of working easiness, efficiency of transmitting output from the vibrator, high torque, and resistance to the wear caused between the rotor and vibrating body.

Figure 3G:
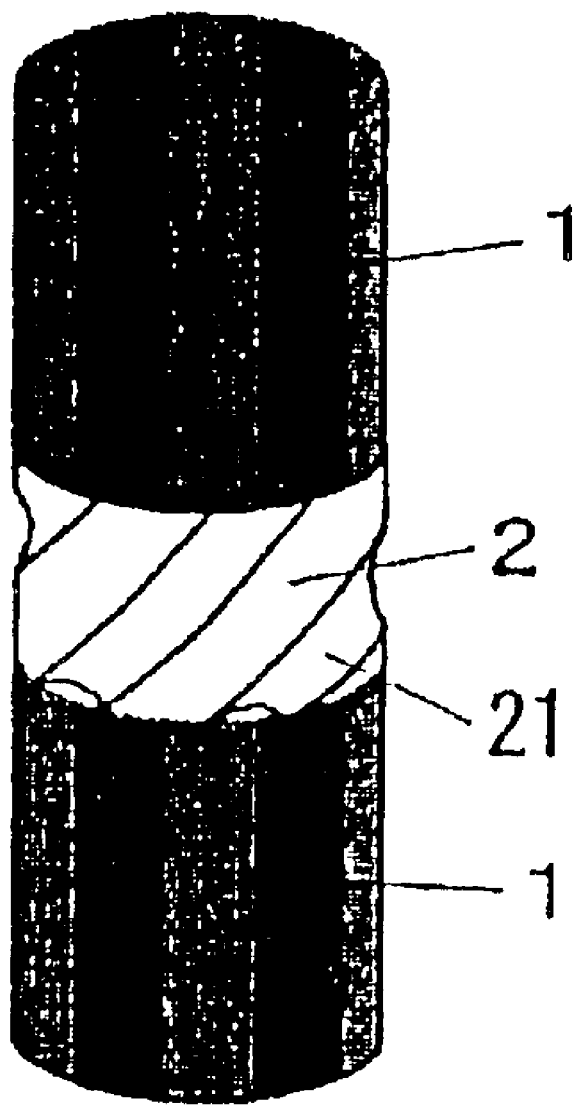

The embodiment shown in FIG. 3G is an embodiment having a different configuration in which not a piezoelectric vibrator 1 but an elastic body 2 is disposed in the middle portion in the longitudinal direction of a vibrating body and piezoelectric vibrators 1 are provided on both sides of the elastic body 2. In this embodiment, a plurality of grooves 21 are provided for the surface of the elastic body 2 located in the middle at a smaller angle than 90 degrees and are provided at equal intervals in the circumferential direction.

This embodiment is characterized in having excellent torsion conversion efficiency and allowing the force of the piezoelectric element with a large volume to be used directly, which allows a high-speed torque motor to be obtained. In addition, this embodiment is excellent in terms of resistance to the wear caused between the rotor and the vibrating body.

Figure 3H:
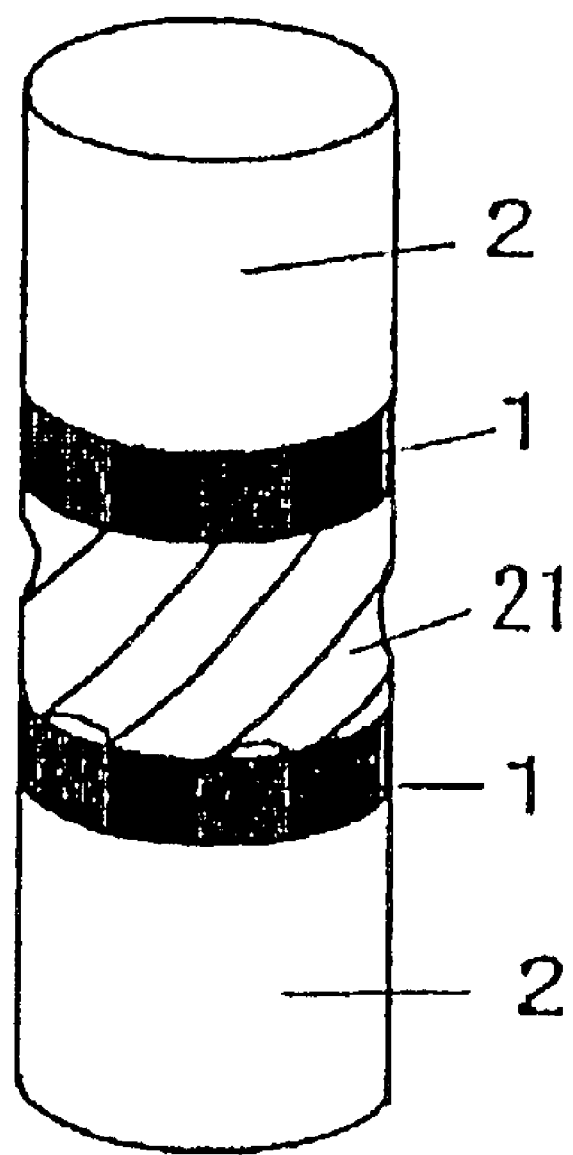

In the embodiment shown in FIG. 3H, an elastic body 2 is disposed in the middle portion in the longitudinal direction of a vibrating body, piezoelectric vibrators 1 are provided on both sides of the elastic body 2, and further elastic bodies 2 are disposed on the outer sides of the piezoelectric vibrators 1. In this embodiment, a plurality of grooves 21 are provided for the surface of the elastic body 2 located in the middle at a smaller angle than 90 degrees and are provided at equal intervals in the circumferential direction.

As in the embodiment shown in FIG. 3G, this embodiment also has excellent torsion conversion efficiency and is suitable as a vibrating body for a motor that is required to rotate at high speed. In addition, this embodiment is excellent in terms of resistance to the wear caused between the rotor and the vibrating body.

Figure 3I:
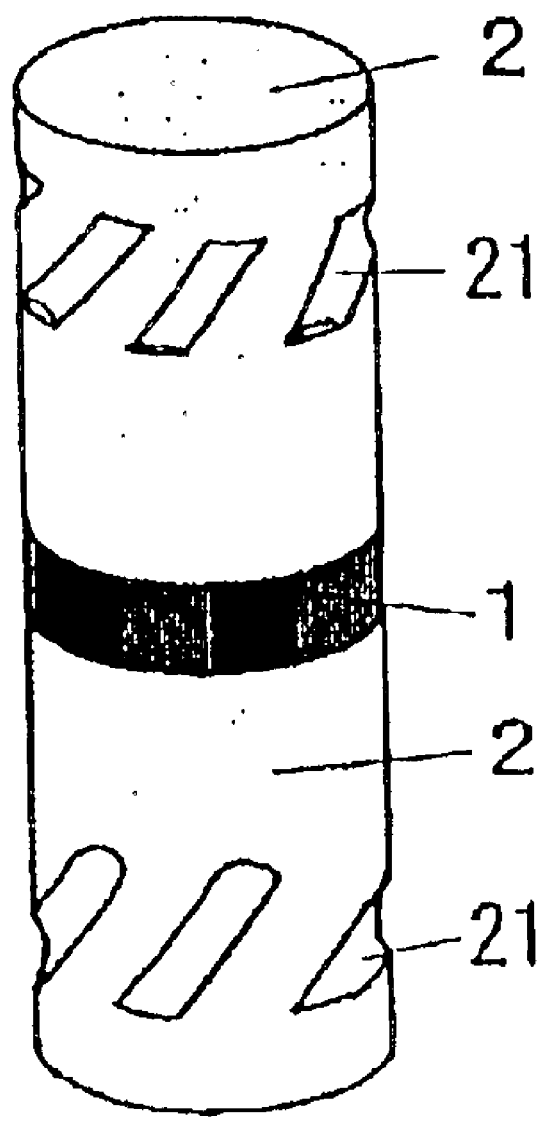

In the embodiment shown in FIG. 3I, a piezoelectric vibrator 1 formed of a piezoelectric element is disposed in the middle portion in the longitudinal direction of a vibrating body and columnar elastic bodies 2 are provided on both sides of the piezoelectric vibrator 1. In this embodiment, a plurality of grooves 21 are provided in the middle portions of the surfaces of the upper and lower elastic bodies 2 at a smaller angle than 90 degrees and are provided at equal intervals in the circumferential direction.

It is preferable that the grooves 21 are provided at locations corresponding to the nodes of standing waves generated in the vibrating body. This embodiment is effective for secondary mode excitation and is also excellent in terms of efficiency of transmitting output from the piezoelectric vibrator and torsion conversion efficiency. In addition, this embodiment can provide high speed and high torque and is also excellent in terms of resistance to the wear caused between the rotor and vibrating body.

Figure 3J:
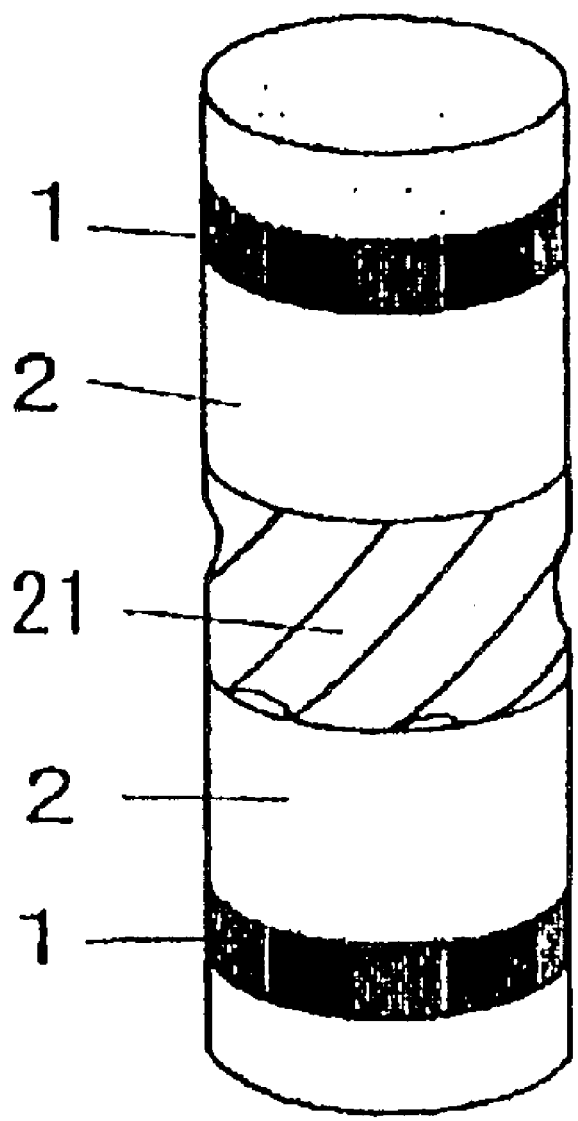

In the embodiment shown in FIG. 3J, an elastic body 2 is disposed in the middle portion in the longitudinal direction of a vibrating body, piezoelectric vibrators 1 are provided on both sides of the elastic body 2, and further elastic bodies 2 are disposed on the outer sides of the piezoelectric vibrators 1. In this embodiment, a plurality of grooves 21 are provided for the surface of the middle portion of the elastic body 2 located in the middle at a smaller angle than 90 degrees and are provided at equal intervals in the circumferential direction. The upper piezoelectric vibrator 1 and the lower piezoelectric vibrator 1 are provided so as to be located symmetrically with respect to the center corresponding to nodes of standing waves generated in the vibrating body. This embodiment is excellent in terms of effectiveness for use of secondary mode and high torsion conversion efficiency and is also excellent in terms of resistance to the wear caused between a rotor and the vibrating body. Furthermore, since the longitudinal vibrations of the piezoelectric vibrators can be used effectively, the electromechanical coupling coefficient is high and thereby high torque is obtained.

The characteristics of the respective embodiments of vibrating body models described above are summarized and shown in the following table.

Embodiment 2

According to the present invention, in a Langevin-type ultrasonic motor having a vibrating body formed of a piezoelectric vibrator and elastic bodies, the vibrating body is provided with a radial projection portion. This allows simplification of the support structure for supporting the vibrating body and a rotor, a pressing mechanism for providing pressing forces between the vibrating body and the rotor, and the conduction structure for bringing piezoelectric vibrator electrodes into conduction. Consequently, a reduction in size of the motor is achieved.

Figure 6:
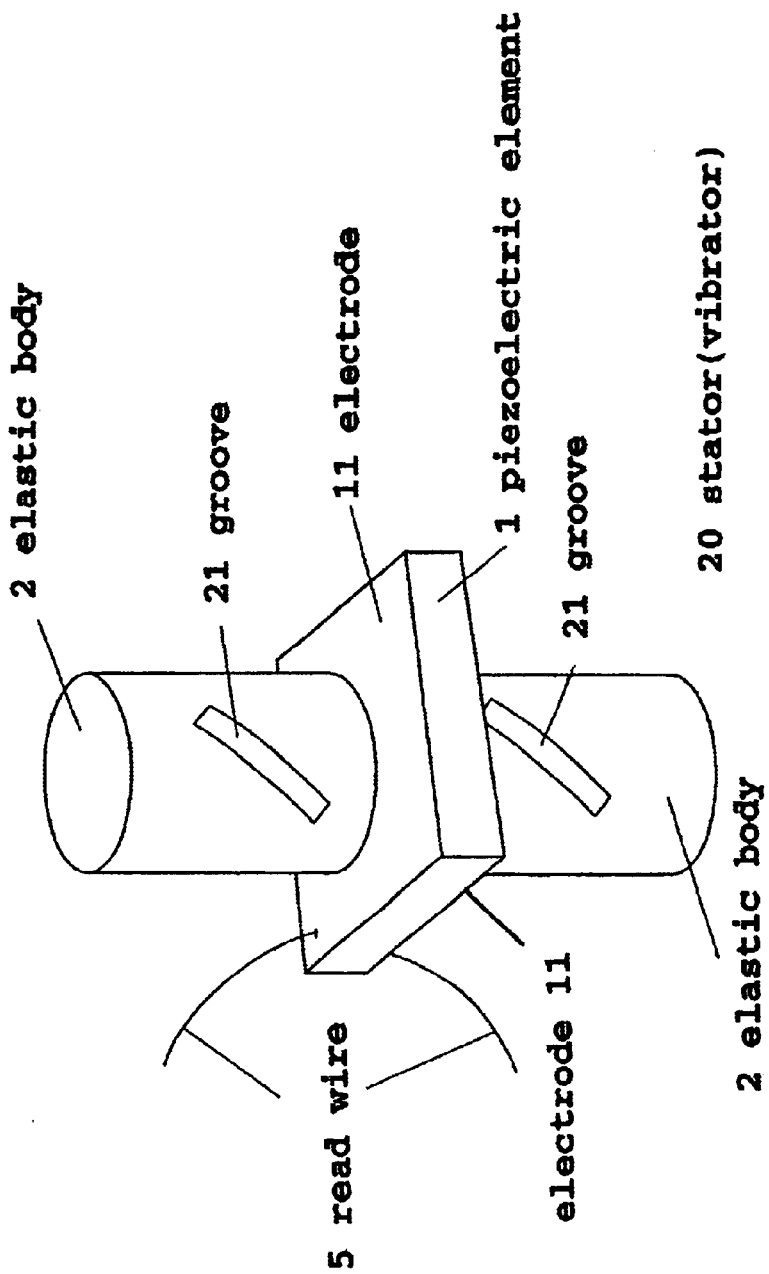
FIG. 6 is a perspective view showing a basic configuration of a stator (a vibrating body) according to the present invention.

FIG. 6 shows a stator (a vibrating body) 20 that is a typical embodiment of the present invention.

This stator 20 employs the following system: only a piezoelectric element 1 polarized in the thickness direction is used as a piezoelectric vibrator, grooves 21 formed in a spiral direction are provided for the surfaces of elastic bodies 2, the displacement in the thickness direction caused by the excitation by the piezoelectric vibrator 1 induces the vibration generated from the combination of a longitudinal vibration and a torsional vibration in the elastic bodies 2, and a rotor (not shown in the drawing) that is brought into contact with the end face of the elastic body 2 is driven by the vibration thus generated.

The stator 20 is designed so that standing waves are generated axially in the elastic bodies 2 that are parts of the stator (the vibrating body) 20 by the piezoelectric vibrator 1. When the grooves 21 are present in the elastic bodies 2, especially in the regions corresponding to nodes of the standing waves, great shearing force acts upon the regions and thereby longitudinal vibrations are converted into the torsional resultant vibrations.

The ultrasonic motor according to the present invention is characterized in that the cross-sectional area (orthogonal to the axial direction) of the piezoelectric vibrator 1 is set to be larger than the cross-sectional area (orthogonal to the axial direction) of the elastic bodies 2. Furthermore, thin films are formed on the respective faces of the piezoelectric vibrator through vapor deposition of, for example, metal and are used as electrodes 11. By employing such a configuration, the stator according to the present invention can be retained without requiring any special support member while the position of its center axis is determined inside a casing through the relationship between the circumferential surface of the piezoelectric vibrator 1 having a larger cross-section and the inner surface of the casing that are in contact with each other.

When the piezoelectric vibrator 1 is formed to have a rectangular cross-section as shown in FIG. 6, it is retained so as not to rotate through the combination with a casing having a rectangular cross-section without requiring any other support member. When the piezoelectric vibrator 1 is formed to have a circular cross-section, it is retained rotatably through the combination with a casing having a circular cross-section without requiring any other support member.

The electrodes 11 of the piezoelectric vibrator 1 sandwiched between and held by the elastic bodies 2 from both sides each have a large cross-section and thus parts of the deposition surfaces are not covered with the elastic bodies 2. Hence, a lead wire 5 can be connected directly to the parts (hereinafter referred to as "a projecting part"). In a conventional configuration, electrodes provided on the upper and lower surfaces of a piezoelectric vibrator are covered by being joined to the elastic bodies. Hence, it was necessary to insert a metal plate or the like between the piezoelectric vibrator and each elastic body to lead terminals to the outside. On the other hand, the present invention allows a lead wire to be connected directly to the exposed deposition surfaces. Consequently, the configuration is simplified and thus a size reduction can be achieved. In addition, loss of vibrations produced between the metal plates and the piezoelectric vibrator or between the metal plates and the elastic bodies can be reduced. Furthermore, the piezoelectric element has a larger diameter than that of a conventional one. This provides an advantage that the output from the motor increases accordingly.

Next, the description is directed to a pressure contact structure employed to apply driving force between the stator and the rotor. The present invention achieves this with the configuration in which the surface of the rotor and the end face of the elastic body 2 are brought into contact with each other axially under pressing forces by an elastic member such as, for example, spring inside the casing.

In the above description, the projecting part of the vibrating body is described as the piezoelectric vibrator. However, another configuration also can be employed in which part of the elastic bodies is formed as the projecting part. In this case, it is desirable that the part be the portion corresponding to nodes of the standing waves generated in the vibrating body.

Concrete embodiments of the present invention are described with reference to FIGS. 7A, 7B, and 7C. First, an example shown in FIG. 7A is described.

Figure 7A:
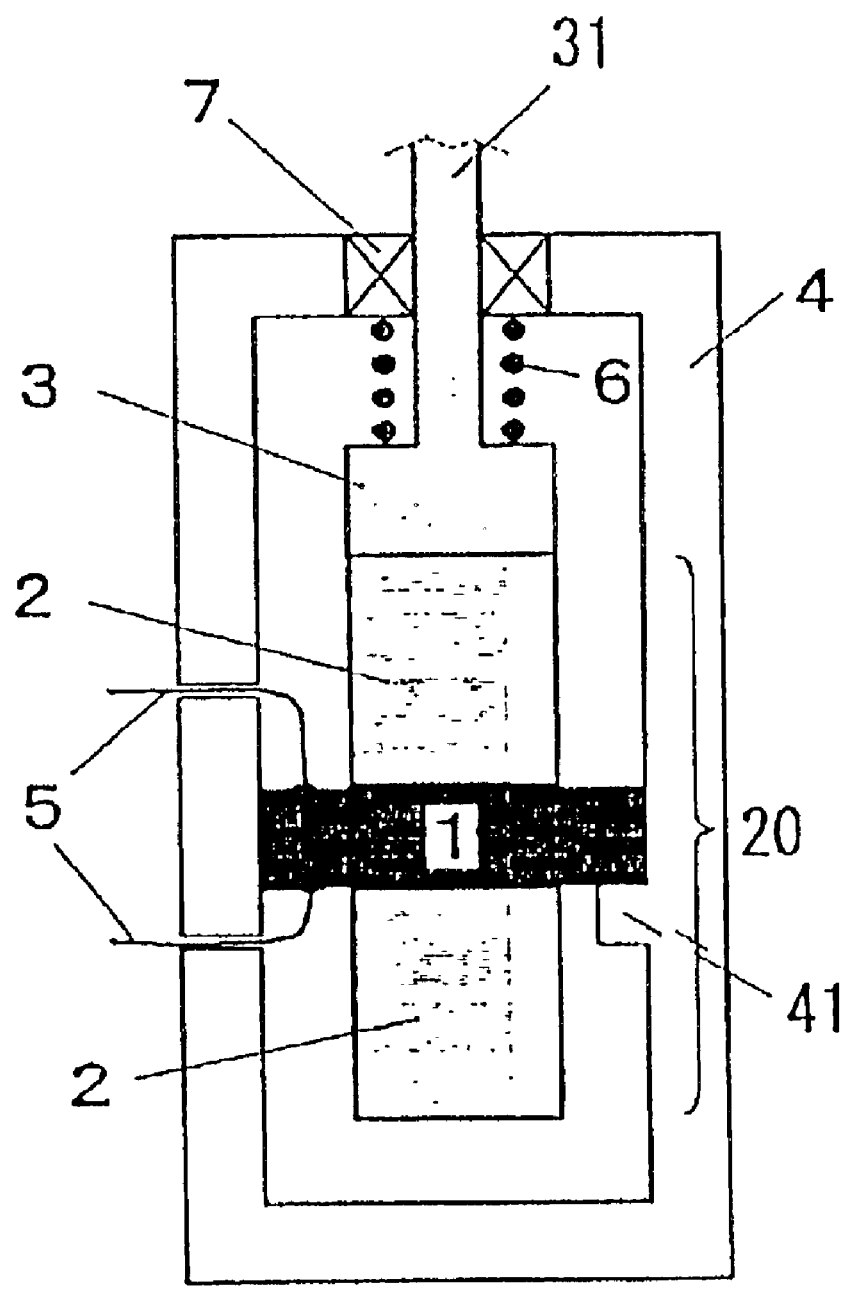
FIGS. 7A to 7C show three embodiments of ultrasonic motors according to the present invention.

An ultrasonic motor shown in FIG. 7A employs a configuration in which a projecting part of a piezoelectric vibrator 1 is engaged with a stepped portion 41 provided inside a casing 4 and the end face of an upper elastic body 2 is in contact with one end face of a rotor 3 having the other end face integrally provided with a drive shaft 31. Furthermore, a spring 6 is provided between the rotor 3 and a radial bearing 7 that supports the drive shaft 31 provided at one end of the casing 4. The stepped portion 41 in this embodiment is formed as a circumferential projection provided on the inner wall surface of the casing 4. However, the stepped portion 41 is not limited thereto and may be one formed in a lower portion with its inner diameter made uniformly smaller.

The piezoelectric element used as the piezoelectric vibrator 1 has a rectangular shape such as one shown in FIG. 6.

When a rectangular shape is employed, a plate-like piezoelectric element can be cut into a piece to be used as the piezoelectric vibrator 1. Hence, not only a reduction in size of the vibrating body can be achieved and a piezoelectric vibrator with a layered structure can be manufactured easily, but also the plate-like piezoelectric element can be used effectively with no portion thereof being wasted. When the stator is contained inside a casing whose inner surface has a rectangular cross-section, the outer periphery of the piezoelectric vibrator 1 comes into contact with the inner surface of the casing 4 and thereby the position of the stator is determined and the piezoelectric vibrator 1 is held by the casing 4 while being prevented from rotating. When consideration is given only to this function of preventing rotation, it is not always necessary that the shape of the piezoelectric vibrator 1 be limited to a rectangular shape. Any other shapes may be employed as long as they are noncircular shapes.

When a drive voltage with a predetermined frequency is applied to the piezoelectric vibrator 1, the piezoelectric vibrator expands and contracts. As a result, the elastic bodies 2 made of an elastic material located on both sides thereof are subjected to longitudinal vibrations and thereby standing waves are generated in the axis direction. Then, the longitudinal vibrations are converted into combined longitudinal-torsional vibrations due to the presence of the grooves 21 provided for the elastic bodies 2. The rotor 3 is disposed so that its end face is brought into contact with the end face of the upper elastic body 2 by being subjected to urging force of the spring 6. Hence, this combined longitudinal-torsional vibrations of the elastic bodies 2 allow the force generated in the torsional direction when the piezoelectric vibrator expands to be transmitted to the rotor 3. The torsional force caused in the opposite direction when the piezoelectric vibrator contracts is difficult to be transmitted since the contraction motion of the piezoelectric vibrator results in a lower frictional force that is generated between the end face of the elastic body 2 and the end face of the rotor 3. Consequently, a torsional force in one direction is transmitted corresponding to the increase and decrease in the frictional force therebetween and thereby the rotor 3 is driven to rotate. This rotational force is conveyed to the outside through the drive shaft 31.

The projecting part and the stepped portion of the casing may be fixed to each other with, for example, an adhesive. In addition, the shape of the casing is not limited to the rectangular shape. The shape may be modified suitably as long as it provides the functions of supporting and fixing the vibrating body 20, the drive shaft 31, and the spring 6 in the present embodiment.

According to the present example, as described above, a size reduction is easy since the support structure and the pressing mechanism in the ultrasonic motor and wiring of the lead wire to the vibrator are simplified.

Embodiment 3

Figure 7B:
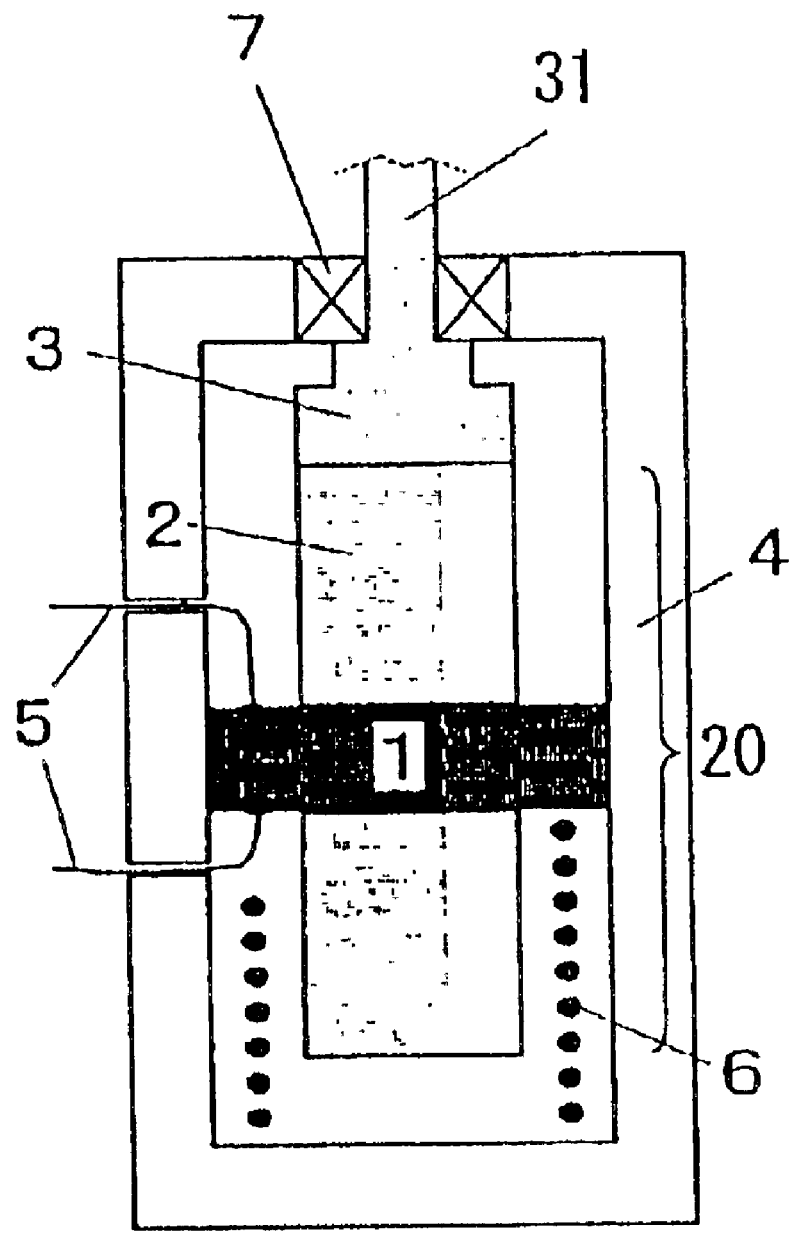

Another embodiment is shown in FIG. 7B.

This ultrasonic motor has a configuration in which no stepped portion is provided inside a casing 4, a spring 6 is disposed in the bottom part to be brought into contact with the lower surface of a projecting part of a piezoelectric vibrator 1 and thereby pushes a stator upward to press a rotor 3 that is in contact with the end face of an upper elastic body 2 against the upper end portion of the casing 4. The piezoelectric vibrator has a rectangular shape as in the aforementioned example. When the stator is contained inside a casing whose inner surface has a rectangular shape, the inner surface of the casing 4 and the outer periphery of the piezoelectric vibrator 1 come into contact with each other and thereby the position of the stator is determined and the piezoelectric vibrator 1 is held by the casing 4 while being prevented from rotating.

When a drive voltage with a predetermined frequency is applied to the piezoelectric vibrator 1, elastic bodies 2 start to undergo combined longitudinal-torsional vibrations and this combined longitudinal-torsional vibrations allow the force produced in the torsional direction when the piezoelectric vibrator 1 expands to be transmitted to the rotor 3. This driving operation is also the same as those in the aforementioned embodiments. This embodiment, however, has a merit of allowing the motor to have a reduced longitudinal size. Similarly in this example, a size reduction is easy since the support structure and the pressing mechanism in the ultrasonic motor and wiring of a lead wire to the vibrator can be simplified.

The shape of the casing is not limited to the rectangular shape. The shape may be modified suitably as long as it provides the functions of supporting and fixing the vibrating body 20, the drive shaft 31, and the spring 6 in the present embodiment as in the aforementioned embodiments. In addition, the projecting part may be provided not for the piezoelectric vibrator but for the elastic bodies 2.

Embodiment 4

Figure 7C:
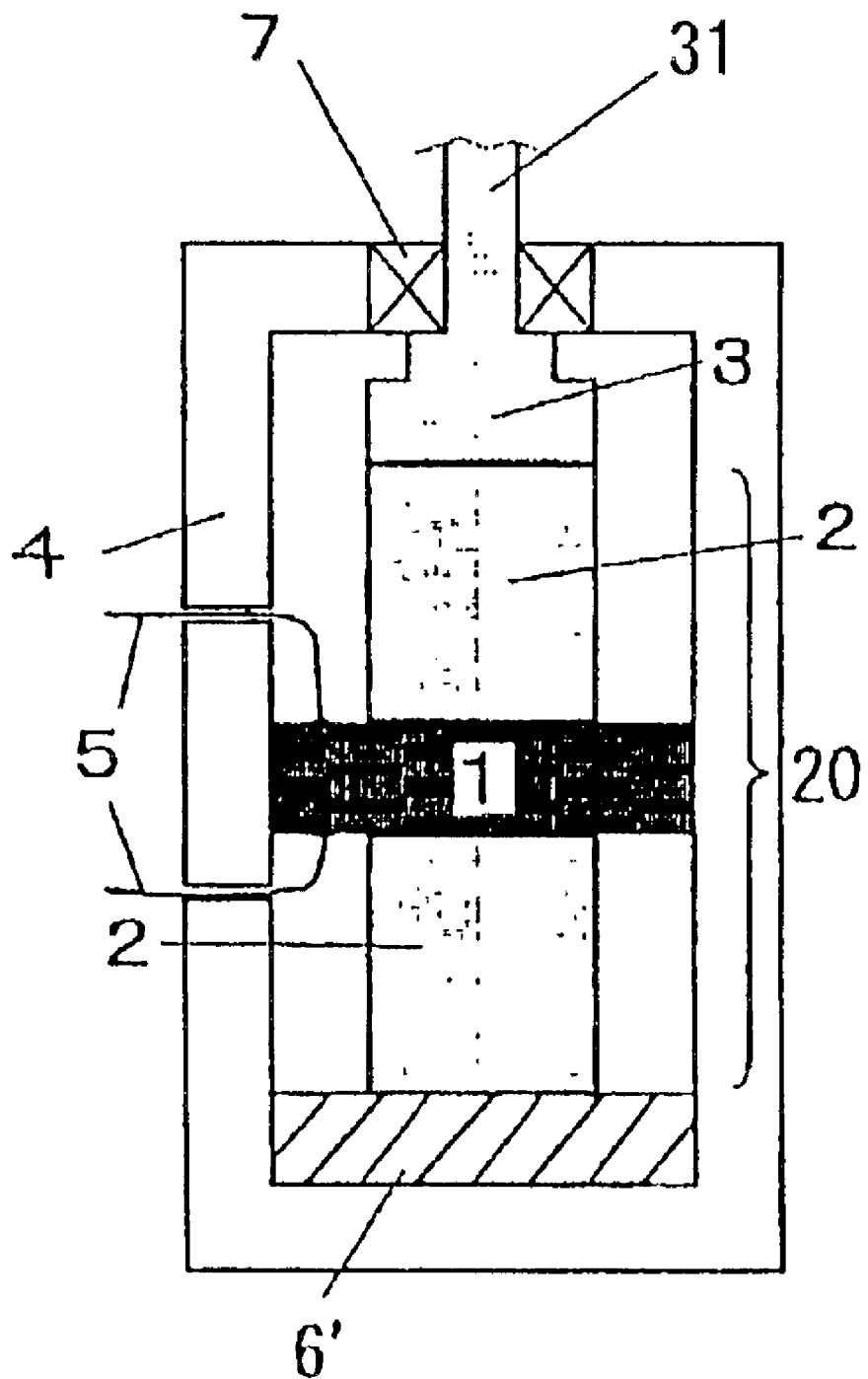

FIG. 7C shows a further embodiment.

This ultrasonic motor is characterized in using an elastic material such as rubber or the like instead of the spring 6 used in Embodiment 3 as a pressing means. This embodiment employs a configuration in which no stepped portion is provided inside a casing 4, an elastic material 6' is disposed at the bottom and is brought into contact with the lower surface of a lower elastic body 2 to push a stator upward and thereby a rotor 3 that is in contact with the end face of an upper elastic body 2 is pressed against the upper end portion of the casing 4. The piezoelectric vibrator has a rectangular shape as in the two embodiments mentioned above. The stator is contained inside a casing whose inner surface has a rectangular cross-sectional shape, so that the inner surface of the casing 4 and the outer periphery of the piezoelectric vibrator 1 are brought into contact with each other and thereby the position of the stator is determined and the piezoelectric vibrator 1 is held by the casing 4 while being prevented from rotating.

When a drive voltage with a predetermined frequency is applied to the piezoelectric vibrator 1, elastic bodies 2 start to undergo combined longitudinal-torsional vibrations and this combined longitudinal-torsional vibrations allow the force produced in the torsional direction when the piezoelectric vibrator 1 expands to be transmitted to the rotor 3. This driving operation is also the same as those in the aforementioned embodiments. Similarly in this embodiment, a size reduction is easy since the support structure and the pressing mechanism in the ultrasonic motor and wiring of a lead wire to the vibrator can be simplified.

The shape of the casing is not limited to the rectangular shape. The shape may be modified suitably as long as it provides the functions of supporting and fixing the vibrating body 20, a drive shaft 31, and the spring 6 in the present embodiment as in the aforementioned embodiments. In addition, the projecting part may be provided not for the piezoelectric vibrator but for the elastic bodies 2.

Embodiment 5

Figure 8A:
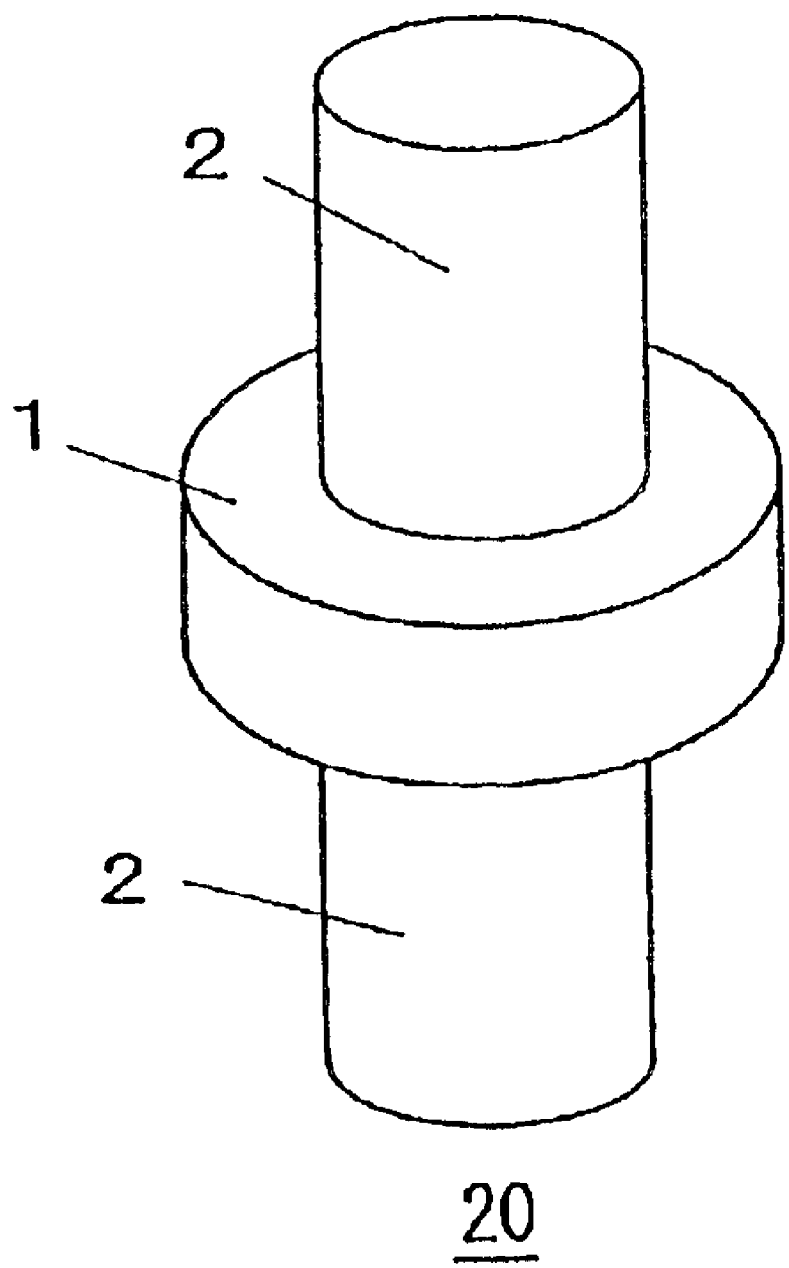
FIGS. 8A to 8C are drawings showing another embodiment of the ultrasonic motor according to the present invention.
Figure 8B:
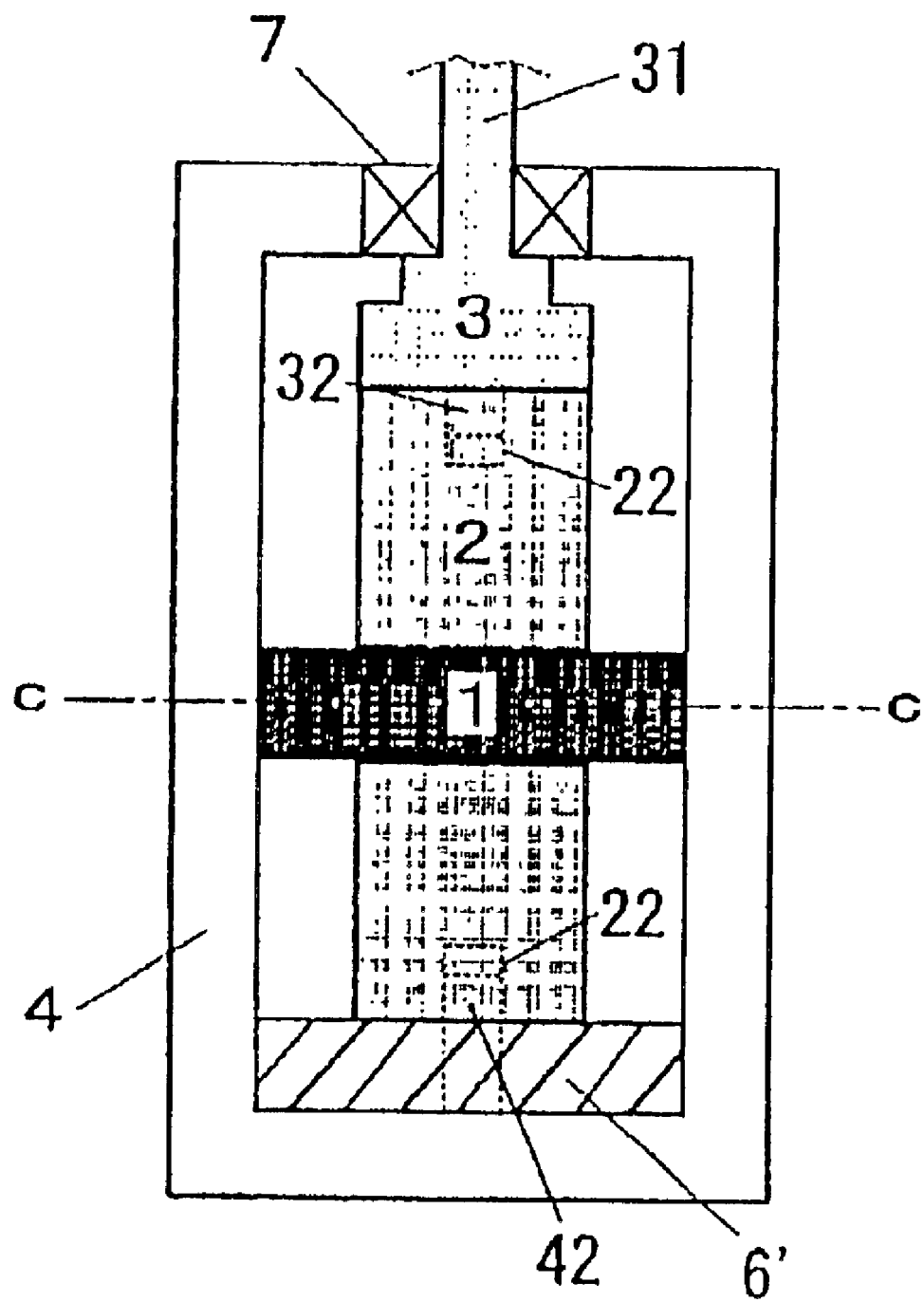
Figure 8C:
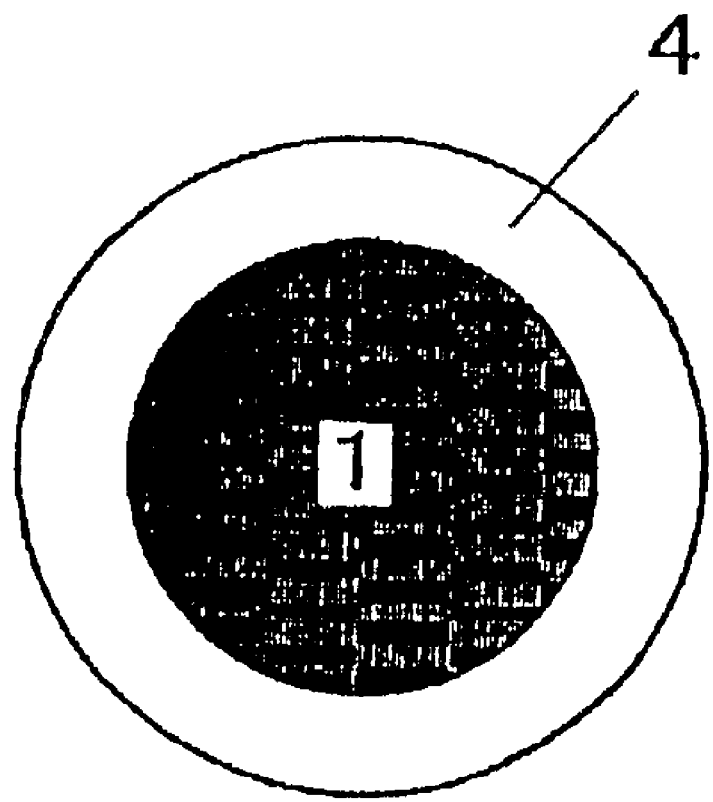

FIGS. 8A to 8C show an example of an ultrasonic motor provided with a piezoelectric vibrator 1 whose cross-section has a circular shape.

Figure 8D:
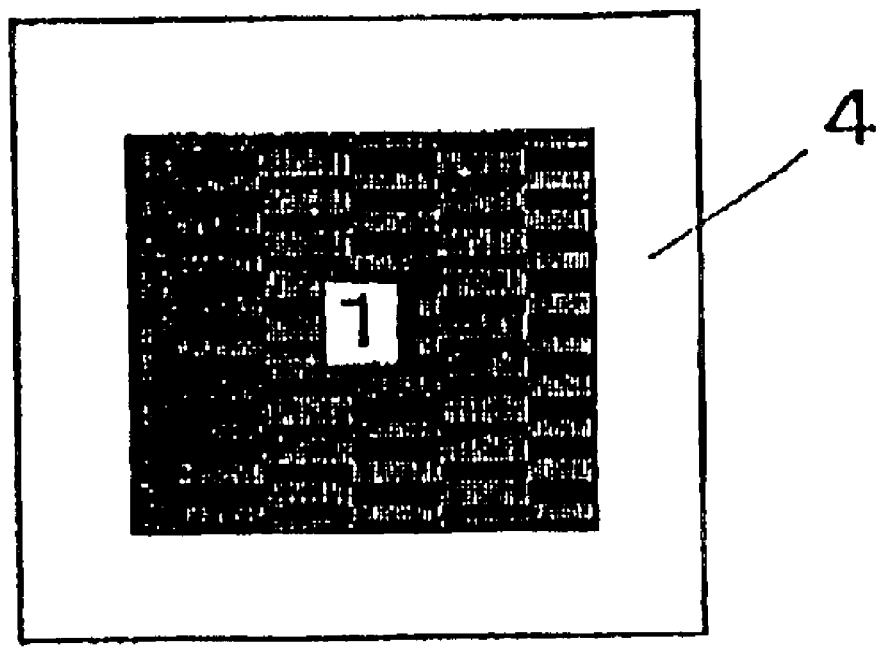
FIG. 8D is a comparative sectional view.
Figure 9:
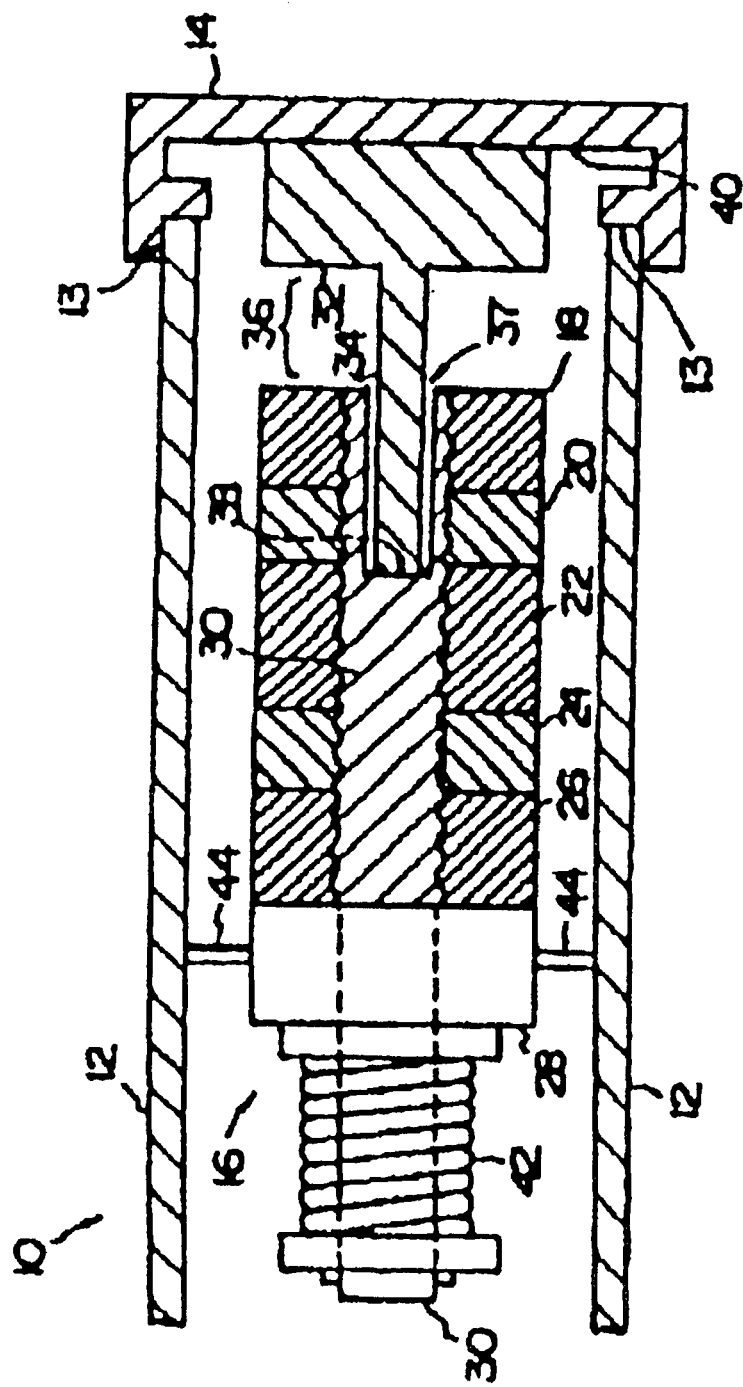
FIG. 9 is a drawing showing the conventional ultrasonic motor.

FIG. 8A shows a perspective view of a vibrating body 20. FIG. 8B shows a sectional view of an ultrasonic motor obtained with the vibrating body 20 contained in a cylindrical casing 4. This embodiment employs a configuration in which an elastic material 6' disposed on one end face of the casing supports the vibrating body and a rotor by pressing them against the other end face of the casing 4, as in the one shown in Embodiment 4. As can be seen from FIG. 8C that is a sectional view taken along line c—c shown in FIG. 8B, the outer periphery of the piezoelectric vibrator 1 and the inner surface of the casing 4 are in contact with each other by their circumferential surfaces. It is difficult to provide these portions with a function of preventing rotation unlike the case of a rectangular vibrator. However, these portions have a function of restricting radial displacement of the vibrating body 20. In this connection, the rectangular cross-section employed in Embodiment 3 is shown in FIG. 8D.

In this embodiment of the ultrasonic motor shown in FIGS. 8A to 8C, the elastic material 6' presses the end face of the lower elastic body 2 to produce the frictional force, which provides a function of preventing rotation. Hence, a fixed portion of the vibrating body is the end face of the lower elastic body 2. In this embodiment, therefore, the sum of the torsional force generated in the upper elastic body 2 and the torsional force generated in the lower elastic body 2 acts on the rotor 3, although the torque that is received by the rotor 3 was only the torsional force produced in the upper elastic body 2 in the aforementioned embodiments.

That is to say, when the vibration modes and phases of the both coincide with each other, a doubled rotational displacement magnitude can be obtained. This embodiment, however, is accompanied with working difficulty in cutting a piezoelectric element into a circular shape and has an aspect that is undesirable in terms of size reduction.

In this embodiment, in order to fix the position of the axial center of the vibrating body, upper and lower axial holes 22 are provided for the center portions of the end faces of the upper and lower elastic bodies 2. Into the upper axial hole 22 is fitted a shaft 32 provided at the center of the rotor 3. Into the lower axial hole 22 is fitted a shaft 42 provided at the center of the bottom of the casing 4. In other words, this mechanism employs a configuration in which the position of the axial center of the vibrating body is determined through the fitting between members that are brought into contact with each other between the end face of the lower elastic body 2 and the casing and between the upper elastic body 2 and the rotor. The end face of the lower elastic body 2 is a fixed part of the vibrating body. The elastic material 6' presses the end face of the lower elastic body 2 to produce frictional force, which provides a function of preventing rotation. The method for providing this function of preventing rotation is not limited to the employment of this configuration. Other methods may be used in which both faces of the elastic material 6' are fixed with an adhesive, or the lower axial hole 22 and the axis 42 provided at the center of the bottom of the casing 4 fitted thereinto are formed to have noncircular shapes. Similarly in this embodiment, a size reduction is easy since the support structure and the pressing mechanism in the ultrasonic motor and wiring of a lead wire to the piezoelectric vibrator can be simplified.

Embodiment 6

Figure 4:
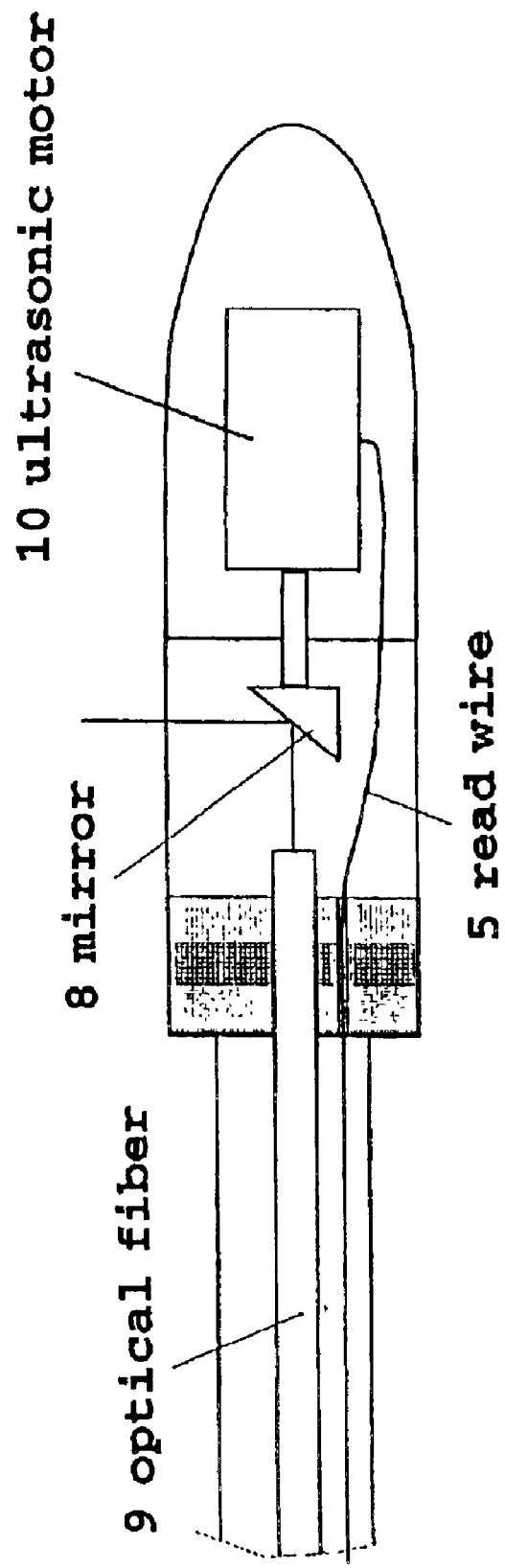
FIG. 4 is a drawing showing an example in which the ultrasonic motor according to the present invention is used in an endoscope.
Figure 5:
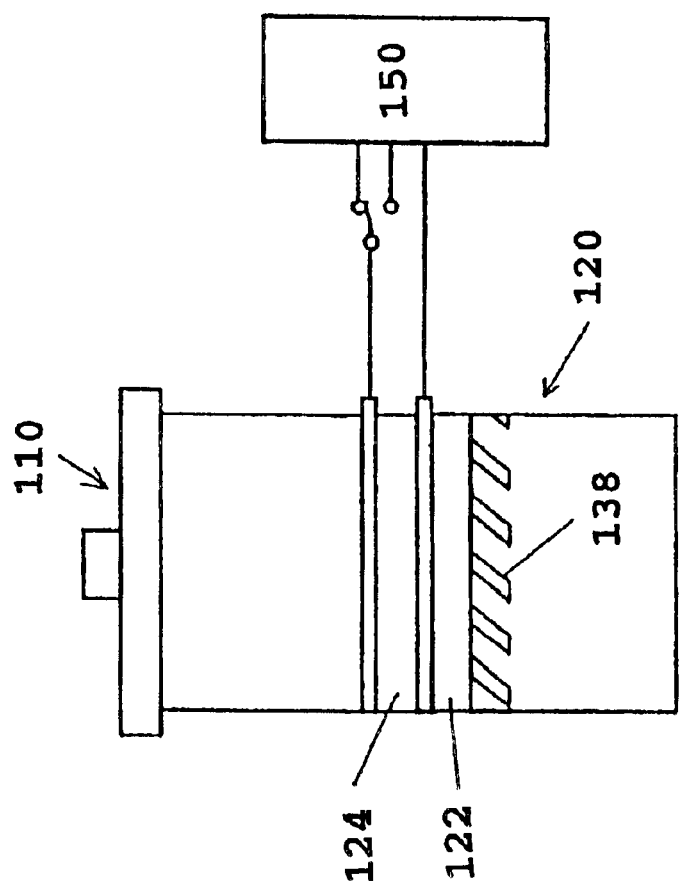
FIG. 5 is a drawing showing a conventional ultrasonic motor.

With reference to FIG. 4, an example is described in which a miniature ultrasonic motor that is made implementable by the present invention is used in an endoscope.

As shown in FIG. 4, a rod-type ultrasonic motor 10 according to the present invention is provided inside the leading portion of an endoscope and a mirror 8 is attached to a drive shaft 31. An optical fiber 9 is passed through a tubular portion of the endoscope. The fiber 9 has functions of guiding light emitted from a light source for illuminating the affected part and transmitting a picture image of the affected part reflected by the mirror 8 to the outside of the body. The mirror 8 is driven to rotate through driving of the miniature ultrasonic motor 10 according to the present invention and thereby the inner surfaces of blood vessels, intestines, and internal organs can be observed over 360 degrees.

In addition to the variety of uses of the miniature ultrasonic motor according to the present invention including the use in an endoscope with a CCD camera attached thereto instead of the mirror, the use for driving a scalpel used for operations or the like, and the use in an ultrasonic autoscope, the miniature ultrasonic motor according to the present invention can be used for the purpose of, for example, observation of a narrow space where no human can enter and inspection of a faucet that is a long and narrow pipe. The ultrasonic motor according to the present invention is of a rod-type, allows a further size reduction, and has a great driving force. Hence, the miniature ultrasonic motor according to the present invention is suitable for use in equipment that is required to be thin or that is provided with an operating part in the leading portion of a long tubular member such as an endoscope.

According to the present invention, in the ultrasonic motor in which a movable body is driven by vibrations of a piezoelectric vibrator and two elastic bodies provided on and under the piezoelectric vibrator, the two elastic members each are provided with grooves and vibrations of the same mode are generated in the elastic bodies disposed on both sides of the piezoelectric vibrator located in the middle. Consequently, no resonance point of frequencies that are close to each other exist, and different vibrations do not influence each other in the case of excitation at a predetermined frequency. Hence, variations in frequency characteristics of the vibrating body are reduced and output power is increased. In addition, even when the frequency of drive voltage to be applied varies slightly, this does not change the state of the influence of vibrations that come closer to each other in accordance with the variation.

The present invention employs a configuration in which the grooves provided for the respective elastic bodies are located symmetrically in the longitudinal direction with respect to the center of the stator and are formed as a plurality of grooves in the same direction at the same angle in both the upper and lower elastic bodies. Hence, the vibrating body as a whole generates one combined longitudinal-torsional vibration and thus the vibration is further simplified.

In the present invention, the grooves provided for the respective elastic bodies are located in regions corresponding to nodes of standing waves generated in the stator. Consequently, when a longitudinal vibration is converted into a combined longitudinal-torsional vibration, large torsional displacement can be caused.

The present invention employs a configuration in which in an ultrasonic motor that drives a movable body by vibrations of vibrating bodies including piezoelectric vibrators formed of a piezoelectric element and an elastic body provided with grooves at least in part that are stacked on top of each other to have a rod shape, the piezoelectric vibrators are disposed in locations corresponding to nodes of standing waves generated in the vibrating bodies and are located symmetrically with respect to the center. Hence, the present invention can provide a high-speed drive ultrasonic motor that has considerably high torsion conversion efficiency.

Furthermore, the present invention employs a configuration in which the grooves provided for the elastic bodies are provided spirally around the vibrating body at least once. According to this configuration, structural uniformity increases and thus no spurious vibration is generated. Furthermore, the elastic bodies have no stress concentration zone. Hence, the ultrasonic motor according to present invention is excellent in terms of fatigue resistance and crashworthiness. In addition, the ultrasonic motor is also excellent in terms of effectiveness for use of a secondary mode, working easiness, efficiency of transmitting output from the vibrator, high torque, and resistance to the wear caused between the rotor and vibrating body.

An ultrasonic motor of the present invention has a vibrating body including a piezoelectric vibrator and an elastic body and drives a rotor by vibrations of the vibrating body. The vibrating body has a projecting part that projects in the radial direction. This projecting part functions as means for preventing the vibrating body from rotating in combination with the shape of the cross section in the axis direction of a casing. Hence, there is no need to prepare any separate member as means for preventing the vibrating body from rotating.

An ultrasonic motor according to the present invention has functions as a member for restricting the radial displacement of the vibrating body in combination with the inner wall surface of the casing and as a member that carries pressing forces exerted by the elastic member disposed in the end portion of the casing in combination with a stepped portion formed on the inner wall of the casing. Hence, there is no need to prepare any separate members. Consequently, the configuration is simple and a size reduction is easy.

An ultrasonic motor according to the present invention has a vibrating body including a piezoelectric vibrator and an elastic body and drives a rotor by vibrations of the vibrating body. The ultrasonic motor ensures a contact between the end face of the vibrating body and the surface of the rotor under pressing forces provided by a pressing means disposed in the end portion of the casing. Hence, there is no need to prepare any separate members. Consequently, the configuration is simple and a size reduction is easy. In addition, the vibrating body has a projecting part that projects in the radial direction of the vibrating body. This projecting part is engaged with a stepped portion formed on the inner wall of the casing and thereby the pressing mechanism provided using a pressing means disposed in the end portion of the casing can be obtained with a simple configuration.

An ultrasonic motor according to present invention has a vibrating body including a piezoelectric vibrator and an elastic body and drives a rotor by vibrations of the vibrating body. The ultrasonic motor has a configuration in which the piezoelectric vibrator has electrodes made of deposition films formed on both faces of a piezoelectric element and a projecting part that projects in the radial direction of the vibrating body, and a lead wire used for applying a drive voltage is connected directly to the projecting part. This ultrasonic motor requires no other electrodes as separate members formed of, for example, metal plates to which a lead wire is connected. Hence, the configuration is simplified and a size reduction can be achieved.

Furthermore, in the present invention, a plate-like piezoelectric element is cut into a rectangular shape to form a piezoelectric vibrator to be used. Hence, the manufacturing process is simple. Consequently, it is easy to achieve a size reduction and to manufacture a layered structure. In addition, no portion is wasted during manufacturing and thus manufacture can be carried out efficiently.

In an ultrasonic motor according to the present invention, there is provided a vibrating body including a piezoelectric vibrator and elastic bodies and the end portion of the lower elastic body prevents the vibrating body from rotating with respect to the casing. In this ultrasonic motor, there is no need to prepare separate members for a support structure and a pressing structure. Hence, the configuration is simple and it is easy to achieve a size reduction. In addition, since the portion fixed to the casing is the end portion of the lower elastic body, not only a torsional vibration of the upper elastic body but also that of the lower elastic body contribute to the rotational drive of the motor, which is a merit. As described above, in any of the methods of supporting the vibrating body according to the present embodiment, the support portion of the vibrating body is not fixed in any directions. Hence, the vibration loss in the support portion is small. This is advantageous especially in size reduction.

The present invention employs a configuration in which the vibrator used in an ultrasonic motor according to the present invention is incorporated into an oscillation circuit to enable the drive by a self-oscillation system. Hence, the ultrasonic motor is not required to have a separate means for supplying voltage to drive the motor. Consequently, a reduction in size of an apparatus can be achieved and the motor is driven stably since the change in resonance frequency due to variations in temperature, voltage, and external load is tracked automatically.

Furthermore, a Langevin-type ultrasonic motor originally has an elongated shape, a reduction in its size can be achieved by the present invention, and it has great driving force. Hence, the ultrasonic motor is suitable for use in equipment that is required to be thinner, for example, equipment that is provided with an operating part in the leading portion of a long tubular member such as an endoscope. The ultrasonic motor can be employed widely as a driving source for an operating part of a variety of electronic apparatuses including diagnostic equipment described above.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

TABLE 1

| Model | Effectiveness for use of Secondary Mode | Fatigue Resistance/ Crashworthiness | Working Easiness | Efficiency of transmitting PZT Output | High Torsional Displacement Conversion Rate | High Torque | Wear Resistance of Rotor and Vibrating Body |
|---|---|---|---|---|---|---|---|
| a | ○ | ◎ |  |  | ○ |  |  |
| b |  |  |  |  | ○ |  | ○ |
| c |  |  |  | ◎ |  | ◎ |  |
| d |  | ○ | ○ | ○ |  | ○ | ○ |
| e |  | ○ | ○ | ○ |  | ○ | ○ |
| f | ○ | ◎ | ○ | ○ |  | ○ | ○ |
| g |  |  |  |  | ◎ | ◎ | ○ |
| h |  |  |  |  | ◎ |  | ○ |
| i | ◎ |  |  | ◎ | ◎ | ○ | ○ |
| j | ◎ |  |  |  | ◎ | ○ | ○ |

What is claimed is:

1. An ultrasonic motor, comprising:
a vibrating body comprised of at least one piezoelectric vibrator having a unidirectional polarization structure and having opposite sides and at least two elastic bodies each connected to a respective one of the opposite sides of the piezoelectric vibrator, each of the elastic bodies having at least one groove formed in a surface of the elastic body and disposed at a preselected angle of 90 degrees or less with respect to a plane extending in a direction generally perpendicular to a longitudinal axis of the vibrating body; and
a movable body frictionally driven by a combination of a longitudinal vibration and a torsional vibration generated by application of a voltage signal to the piezoelectric vibrator of the vibrating body.

2. An ultrasonic motor according to claim 1; wherein the grooves are disposed symmetrically with respect to a central axis of the vibrating body extending generally perpendicular to the longitudinal axis thereof.

3. An ultrasonic motor according to claim 1; wherein each of the elastic bodies has an end surface; and wherein the grooves are formed in any surface of the elastic bodies other than the end surfaces thereof.

4. An ultrasonic motor according to claim 1; wherein the at least one groove formed in the surface of each of the elastic bodies comprises a plurality of grooves disposed in the same direction and at the same preselected angle.

5. An ultrasonic motor according to claim 1; wherein the grooves are disposed in regions of the elastic bodies corresponding to nodes of standing waves generated in the vibrating body upon application of a voltage signal to the piezoelectric vibrator.

6. An ultrasonic motor according to claim 1; wherein the at least two elastic bodies comprises a plurality of elastic bodies stacked along the longitudinal axis to define a generally rod-shaped vibrating body; and wherein the at least one piezoelectric vibrator comprises a plurality of piezoelectric vibrators disposed symmetrically along the longitudinal axis with respect to a center of the vibrating body, the piezoelectric vibrators being connected to the elastic bodies at regions corresponding to nodes of standing waves generated in the vibrating body upon application of driving signals to the piezoelectric vibrators.

7. An ultrasonic motor according to claim 1; wherein the grooves are generally spiral-shaped.

8. An ultrasonic motor, comprising:
a vibrating body comprised of at least one piezoelectric vibrator having a unidirectional polarization structure and having opposite sides and a projecting part extending transverse to a longitudinal axis of the vibrating body, and at least two elastic bodies each connected with a respective one of the opposite sides of the piezoelectric vibrator, each of the elastic bodies having at least one groove formed in a surface of the elastic body and disposed at a preselected angle of 90 degrees or less with respect to a plane extending in a direction generally perpendicular to the longitudinal axis of the vibrating body; and
a movable body frictionally driven by a combination of a longitudinal vibration and a torsional vibration generated by applying a driving signal to the piezoelectric vibrator of the vibrating body.

9. An ultrasonic motor according to claim 8; further comprising a casing for containing the vibrating body so that the projecting part of the piezoelectric vibrator engages the casing for restraining rotational movement of the piezoelectric vibrator.

10. An ultrasonic motor according to claim 8; further comprising a casing for containing the vibrating body and an elastic member disposed between the projecting part of the piezoelectric vibrator and the casing.

11. An ultrasonic motor according to claim 8; further comprising a casing for containing the vibrating body and an elastic member disposed between the vibrating body and the casing.

12. An ultrasonic motor according to claim 8; further comprising a plurality of electrodes disposed on the projecting part of the piezoelectric vibrator for applying a voltage signal to the piezoelectric vibrator to drive the vibrating body.

13. An ultrasonic motor according to claim 11; wherein the vibrating body has a central hole extending along a central axis thereof.

14. An ultrasonic motor according to claim 8; wherein the entire projecting part forms part of the piezoelectric vibrator for receiving the voltage.

15. In an electronic apparatus having a rotational member, an ultrasonic motor according to claim 1 for rotationally driving the rotational member.

16. In an electronic apparatus having a rotational member, an ultrasonic motor according to claim 8 for rotationally driving the rotational member.

17. An ultrasonic motor comprising:
a piezoelectric vibrator having a unidirectional polarization structure and being driven by a voltage signal to undergo expansion and compression movement;
at least two elastic bodies connected to opposite ends of the piezoelectric vibrator and vibrationally driven by the expansion and compression movement of the piezoelectric vibrator, each of the elastic bodies having at least one groove formed in a surface thereof for converting the expansion and compression movement of the piezoelectric vibrator into torsional vibration so that the elastic bodies generate a combination of longitudinal vibration and torsional vibration; and a movable member connected to the elastic bodies to be frictionally driven by the combination of longitudinal and torsional vibrations generated by the elastic bodies.

18. An ultrasonic motor according to claim 17; wherein the each of the grooves is disposed at an angle of 90 degrees or less with respect to a plane extending in a direction generally perpendicular to a longitudinal axis of the corresponding elastic body.

19. An ultrasonic motor according to claim 17; wherein the grooves comprises spiral grooves.

20. An ultrasonic motor according to claim 17; wherein the at least one groove of each of the elastic bodies comprises a plurality of spiral grooves.

21. An ultrasonic motor according to claim 17; wherein the grooves are formed in portions of the surfaces of the elastic bodies that are in contact with the piezoelectric vibrator.

22. An ultrasonic motor according to claim 17; wherein each of the elastic bodies has an inner end portion connected to the piezoelectric vibrator and an outer end portion; and wherein the grooves are formed in the surface of the elastic bodies at the outer end portions thereof.

23. An ultrasonic motor according to claim 17; wherein the grooves are formed in generally central surface portions of the elastic bodies.

24. An ultrasonic motor according to claim 17; wherein each of the elastic bodies is generally square-shaped in cross-section.

25. An ultrasonic motor according to claim 17; wherein each of the elastic bodies has an inner end portion connected to the piezoelectric vibrator and an outer end portion; and wherein each of the grooves extends from the inner end portion to the outer end portion of the respective one of the elastic bodies.

26. An ultrasonic motor according to claim 17; wherein the piezoelectric element has a portion projecting outwardly in a direction transverse to the surfaces of the elastic bodies.

27. An ultrasonic motor according to claim 26; further comprising a case member containing the elastic bodies and the piezoelectric vibrator so that the projecting portion of the piezoelectric vibrator contacts the case member for restraining rotational movement of the piezoelectric vibrator.

28. An ultrasonic motor comprising:

a pair of piezoelectric vibrators each having a unidirectional polarization structure and being driven by a voltage signal to undergo expansion and compression movement;

an elastic body disposed between and connected to the piezoelectric vibrators and vibrationally driven by the expansion and compression movement of the piezoelectric vibrators, the elastic body having at least one groove formed in a surface thereof for converting the expansion and compression movement of the piezoelectric vibrators into torsional vibration so that the elastic body generates a combination of longitudinal vibration and torsional vibration; and a movable member connected to the elastic body to be frictionally driven by the combination of longitudinal and torsional vibrations generated by the elastic body.

29. An ultrasonic motor according to claim 28; wherein the elastic body comprises a first elastic body, each of the piezoelectric vibrators having a first end connected to the first elastic body and a second end; and further comprising second and third elastic bodies each connected a respective one of the second ends of the piezoelectric vibrators.

30. An ultrasonic motor according to claim 28; wherein the groove is disposed at an angle of 90 degrees or less with respect to a plane extending in a direction generally perpendicular to a longitudinal axis of the elastic body.

* * * * *